(12) United States Patent
Tanaka

(10) Patent No.: US 9,720,009 B2
(45) Date of Patent: Aug. 1, 2017

(54) SAMPLE PROCESSING APPARATUS, SAMPLE RACK SET, AND SAMPLE PROCESSING METHOD

(71) Applicant: Sysmex Corporation, Kobe-shi, Hyogo (JP)

(72) Inventor: Toshihisa Tanaka, Kobe (JP)

(73) Assignee: SYSMEX CORPORATION, Kobe (JP)

(*) Notice: Subject to any disclaimer, the term of this patent is extended or adjusted under 35 U.S.C. 154(b) by 0 days.

(21) Appl. No.: 14/198,052

(22) Filed: Mar. 5, 2014

(65) Prior Publication Data
US 2014/0256050 A1 Sep. 11, 2014

(30) Foreign Application Priority Data
Mar. 7, 2013 (JP) .................... 2013-045818

(51) Int. Cl.
*G01N 35/04* (2006.01)
*G01N 35/02* (2006.01)
*B01L 9/02* (2006.01)
*B01L 3/00* (2006.01)
(Continued)

(52) U.S. Cl.
CPC ......... *G01N 35/026* (2013.01); *B01L 3/5453* (2013.01); *B01L 9/06* (2013.01);
(Continued)

(58) Field of Classification Search
CPC .............. G01N 35/026; G01N 35/02; G01N 35/00584; G01N 2035/0415; G01N 2035/0412; G01N 2035/0401; G01N 2035/04; G01N 2035/00752; G01N 2035/00702; G01N 2035/00524; G01N 2035/00465; B01L 3/5453; B01L 3/545; B01L 3/54; B01L 3/00; B01L 9/06; B01L 9/00; B01L 2300/02; B01L 2300/00; Y10T 436/113332; Y10T 436/11; Y10T 436/00
USPC .................. 436/47, 43; 422/65, 63, 50
See application file for complete search history.

(56) References Cited

U.S. PATENT DOCUMENTS

| 5,985,215 A | 11/1999 | Sakazume et al. |
| 6,156,575 A | 12/2000 | Fassbind et al. |

(Continued)

FOREIGN PATENT DOCUMENTS

| CN | 101126764 A | 2/2008 |
| CN | 102023110 A | 4/2011 |

(Continued)

*Primary Examiner* — Christine T Mui
(74) *Attorney, Agent, or Firm* — Brinks Gilson & Lione

(57) ABSTRACT

A sample processing apparatus comprises a transporting section configured to transport a sample rack that is capable of holding a sample container at a plurality of holding positions, a detecting section that is configured to detect presence or absence of a rack distinction member at a holding position of the sample rack, an aspirating section that is configured to aspirate a sample in the sample container, and a control section that is configured to control an aspirating operation of the aspirating section. The control section changes an aspirating operation with respect to the sample container held in the sample rack based on the presence/absence of the rack distinction member at the holding position of the sample rack.

22 Claims, 21 Drawing Sheets

(51) Int. Cl.
*B01L 9/06* (2006.01)
*G01N 35/00* (2006.01)

(52) U.S. Cl.
CPC ....... *G01N 35/00584* (2013.01); *G01N 35/02* (2013.01); *B01L 2300/02* (2013.01); *G01N 2035/00524* (2013.01); *G01N 2035/00752* (2013.01); *G01N 2035/0415* (2013.01); *Y10T 436/113332* (2015.01)

(56) References Cited

U.S. PATENT DOCUMENTS

| | | | |
|---|---|---|---|
| 2006/0292038 A1* | 12/2006 | Johansson | G01N 35/025 422/82.05 |
| 2008/0050279 A1 | 2/2008 | Fujita | |
| 2011/0073438 A1* | 3/2011 | Takai | 198/367 |
| 2011/0076668 A1* | 3/2011 | Oguro | G01N 35/026 435/2 |
| 2012/0028343 A1 | 2/2012 | Kitagawa | |
| 2013/0125628 A1* | 5/2013 | Kitagawa | G01N 33/49 73/61.41 |

FOREIGN PATENT DOCUMENTS

| | | | | |
|---|---|---|---|---|
| EP | 0 152 610 A2 | 8/1985 | | |
| EP | 1 890 156 A2 | 2/2008 | | |
| JP | 10-123147 A | 5/1998 | | |
| JP | H10-123147 A | 5/1998 | | |
| JP | 2008-46033 A | 2/2008 | | |
| JP | 2011-253290 | * 11/2011 | ............ | G01N 35/02 |
| JP | 2012-173251 A | 9/2012 | | |
| WO | WO 94/14073 A1 | 6/1994 | | |

* cited by examiner

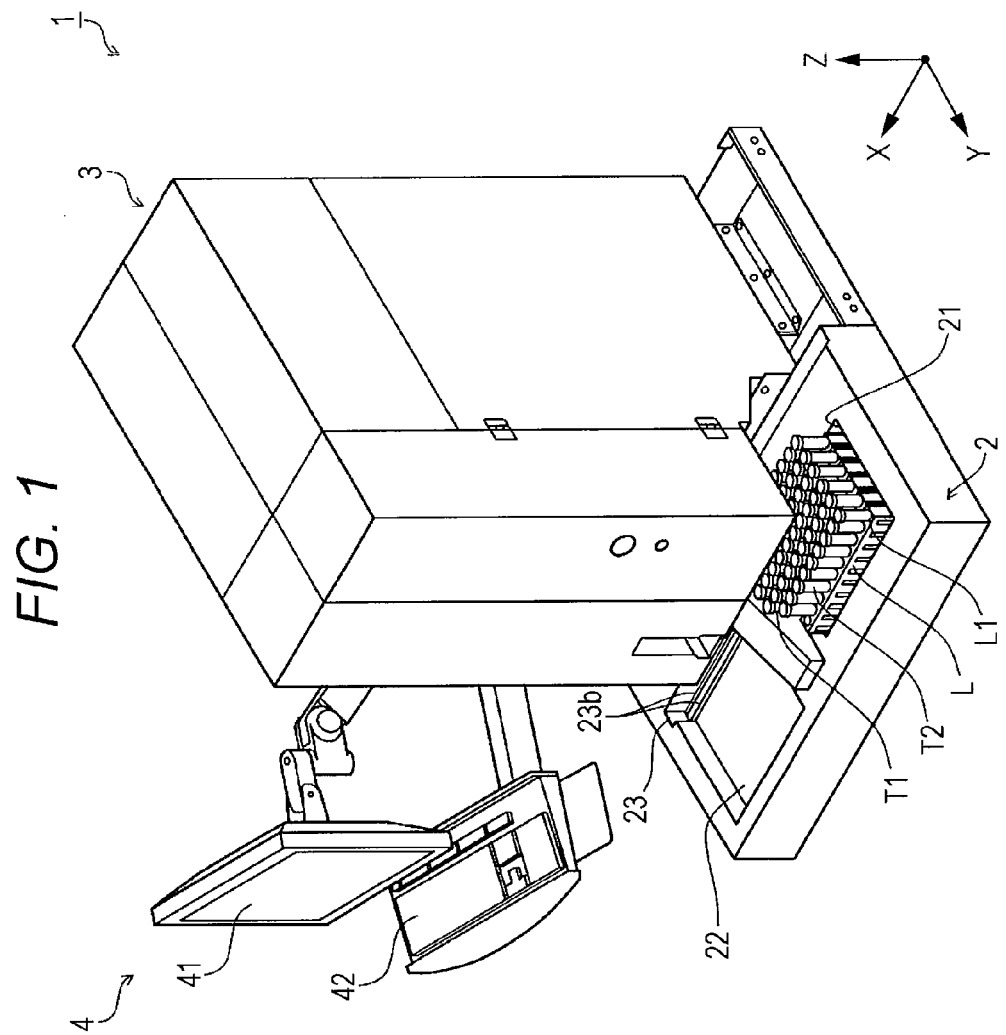

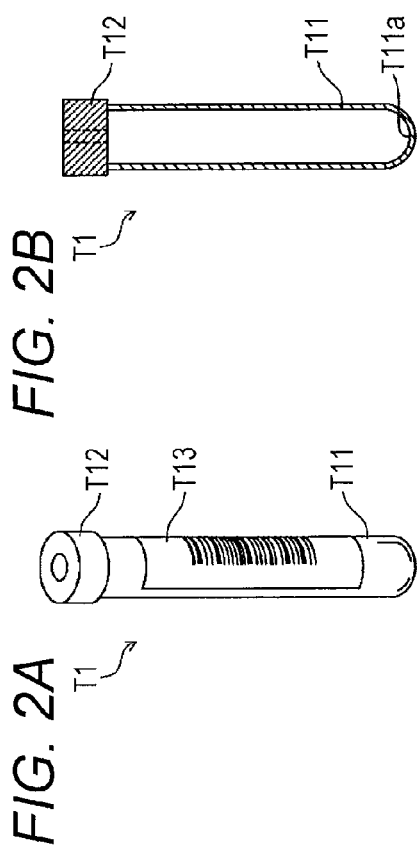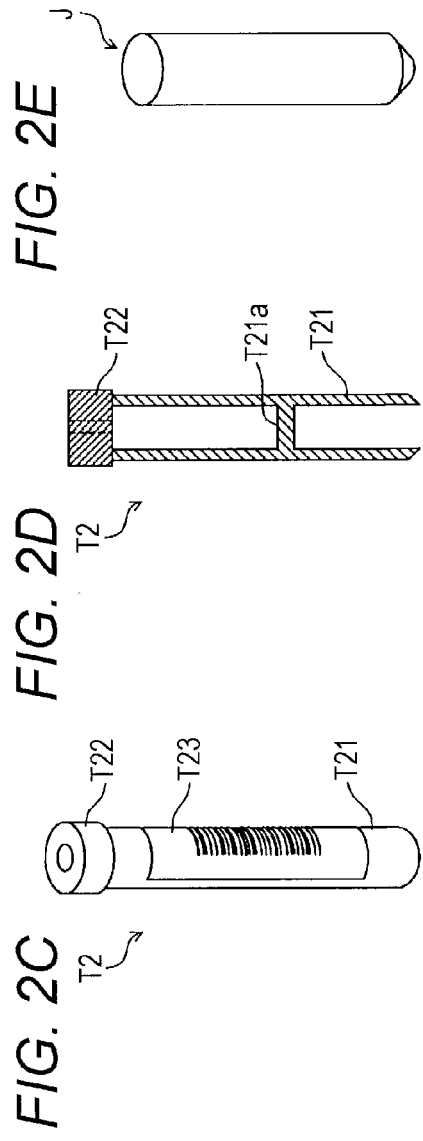

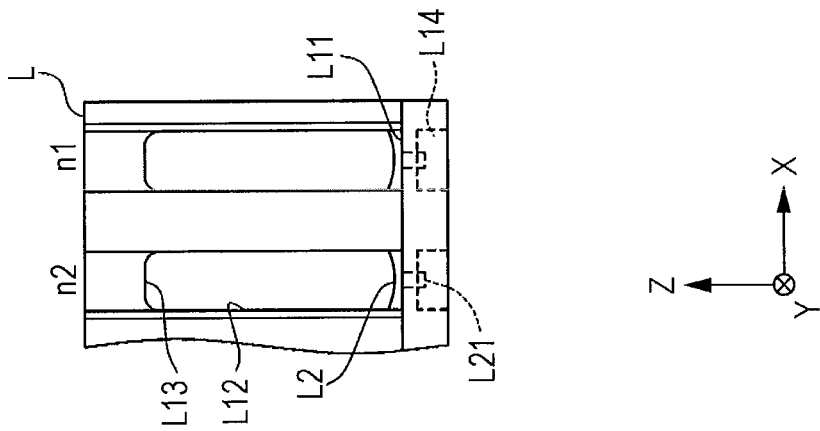
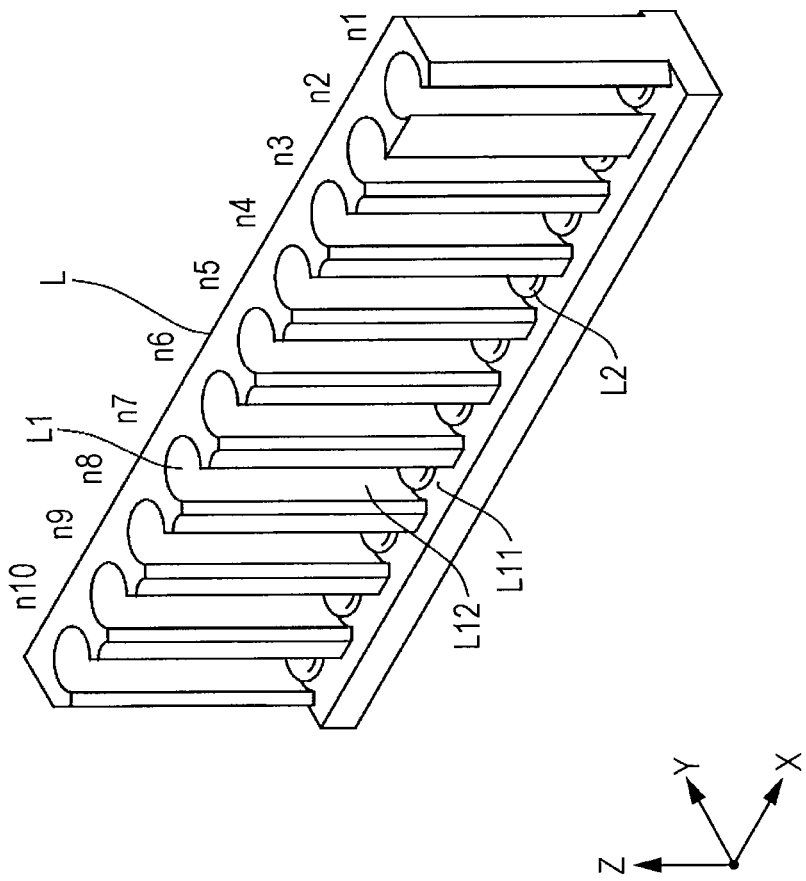

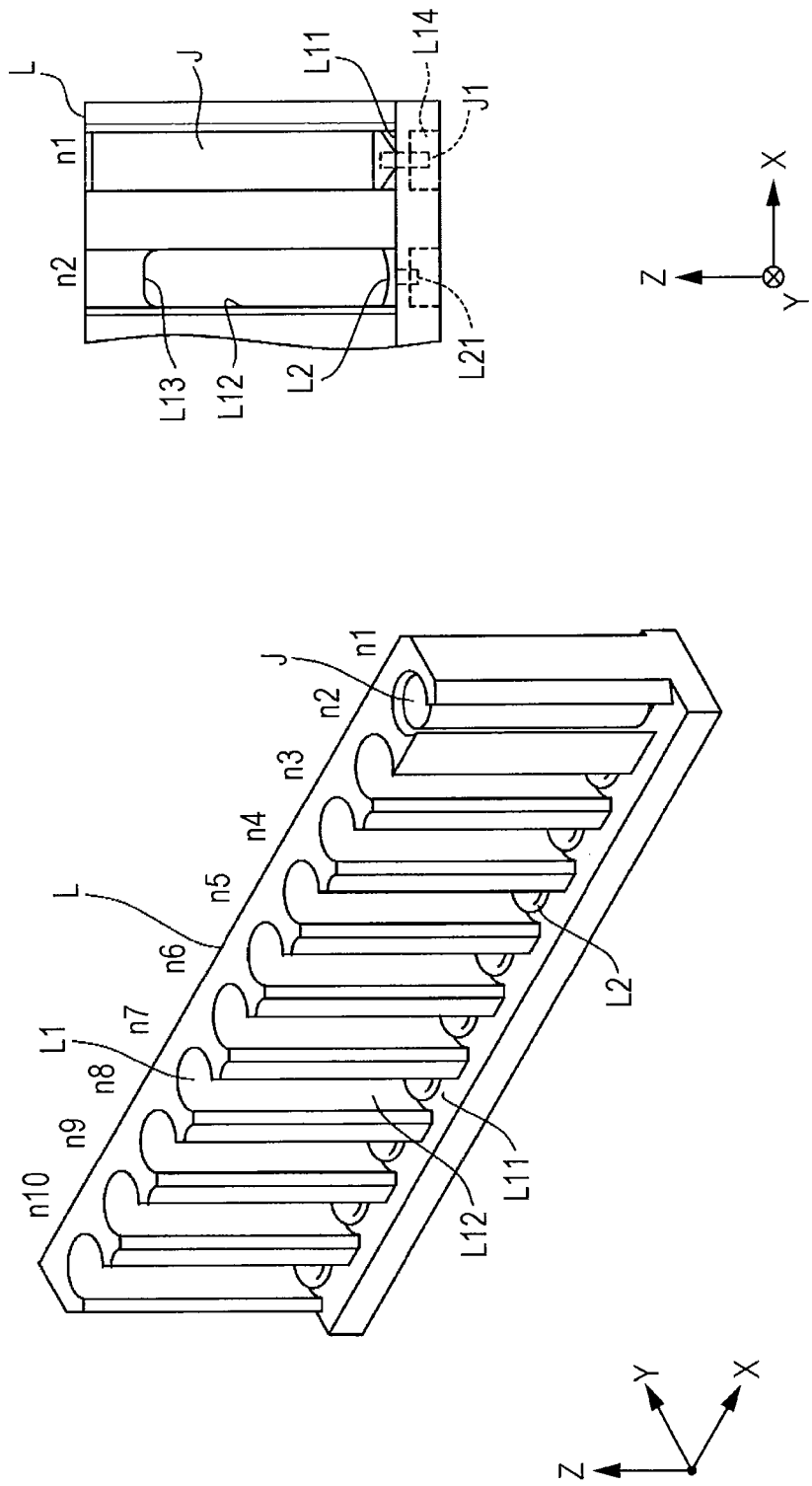

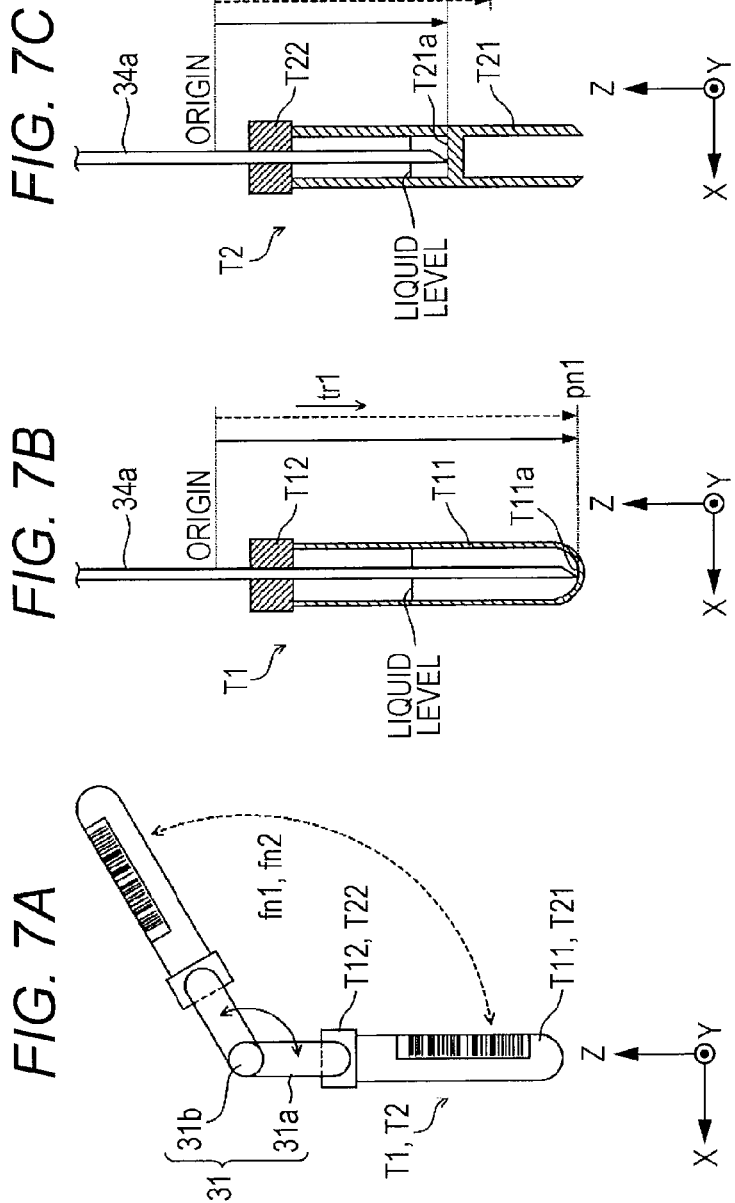

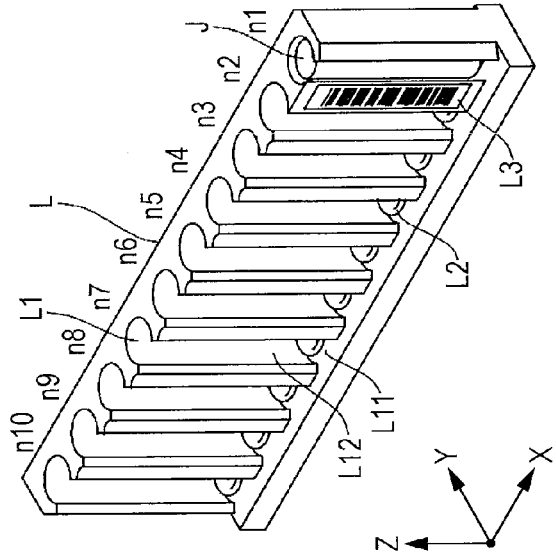
FIG. 11A
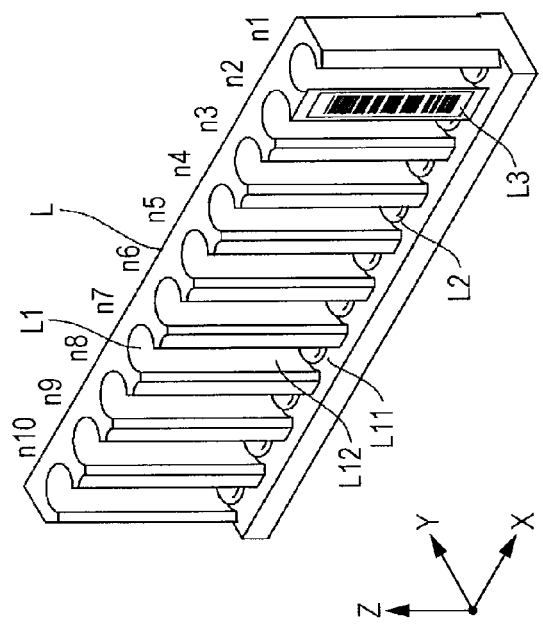
FIG. 11B
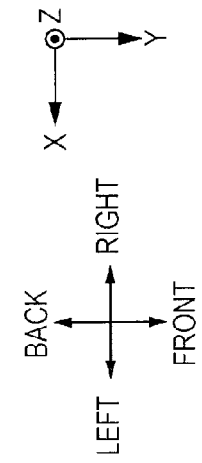
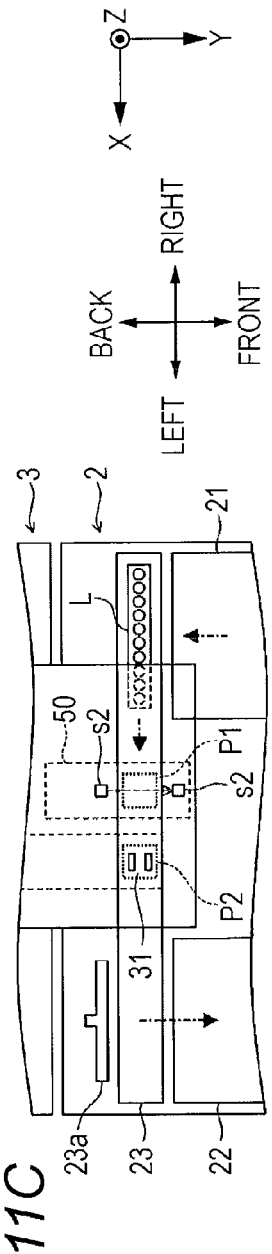
FIG. 11C

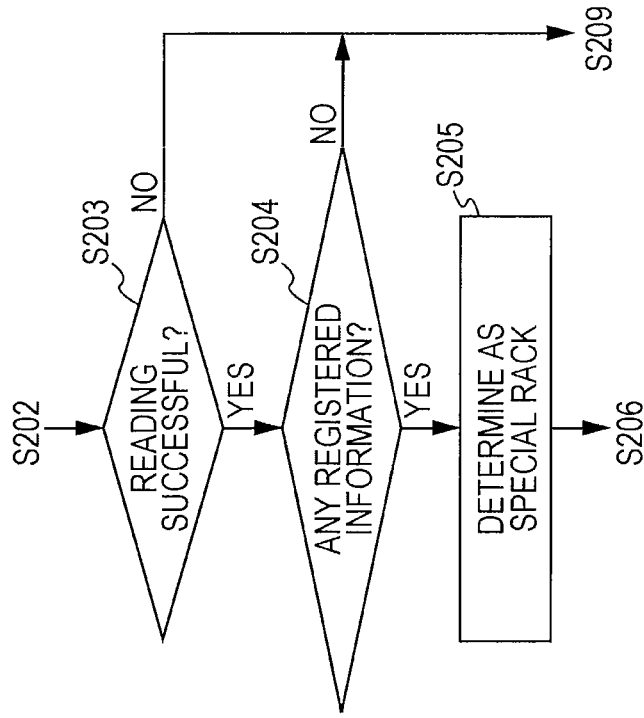

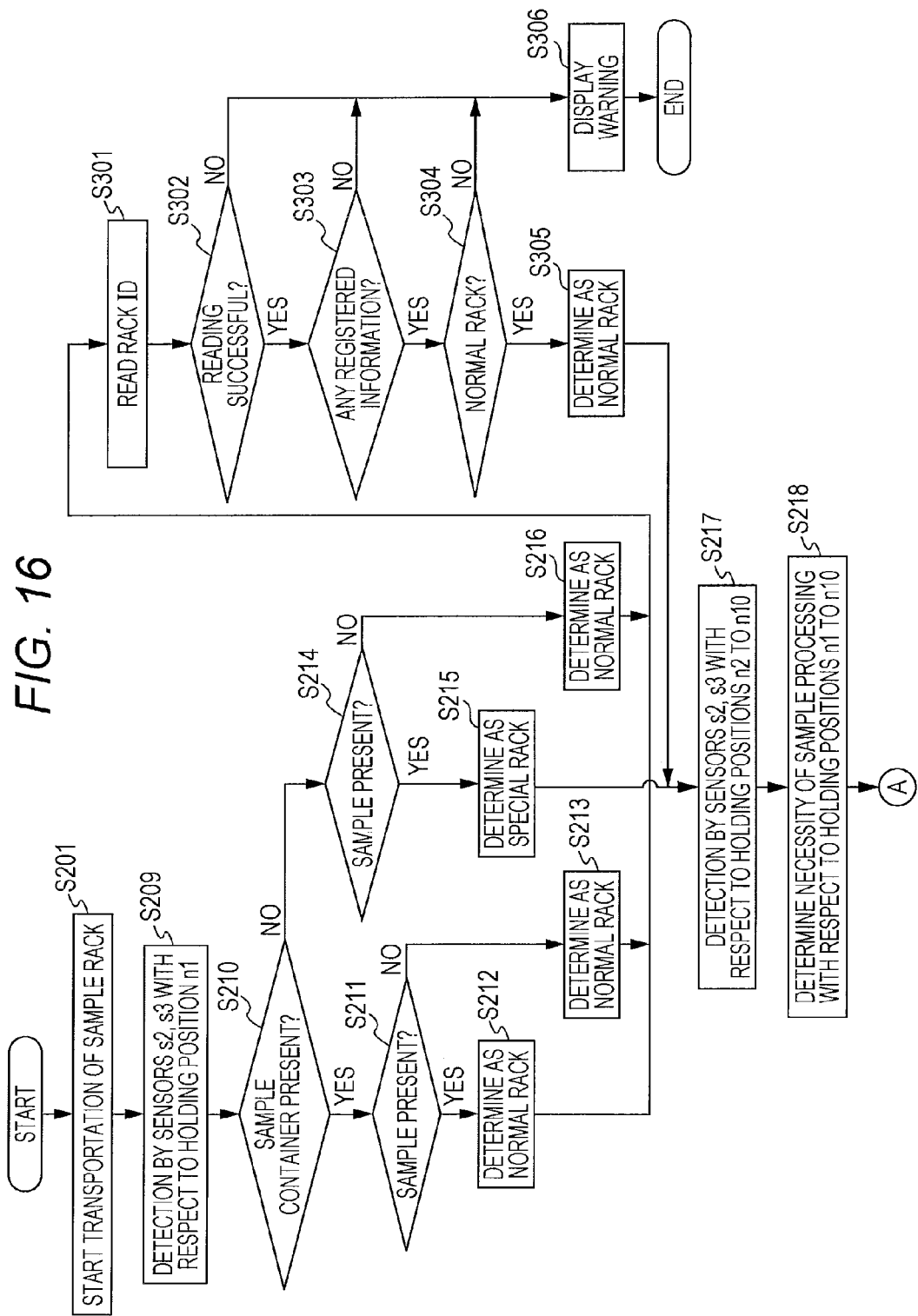

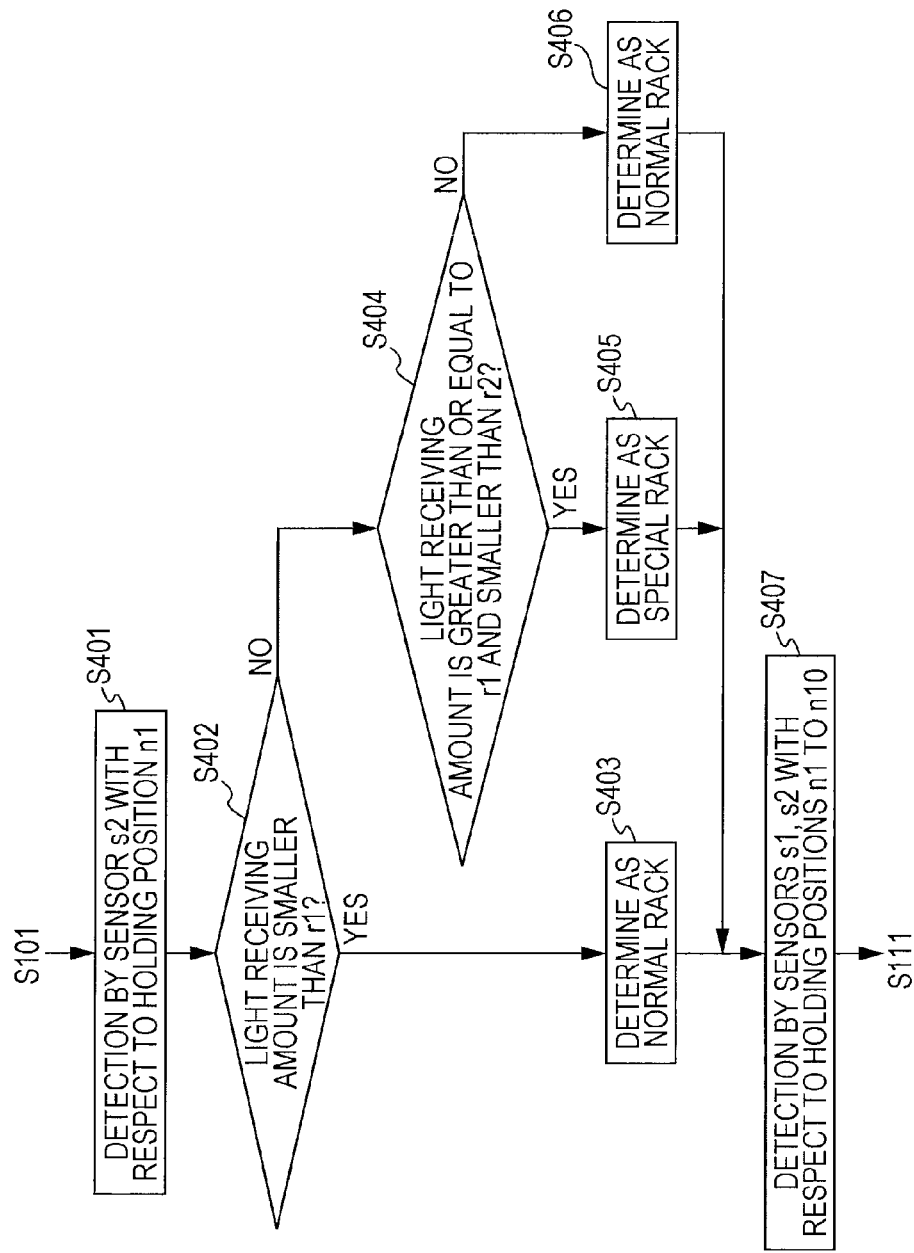

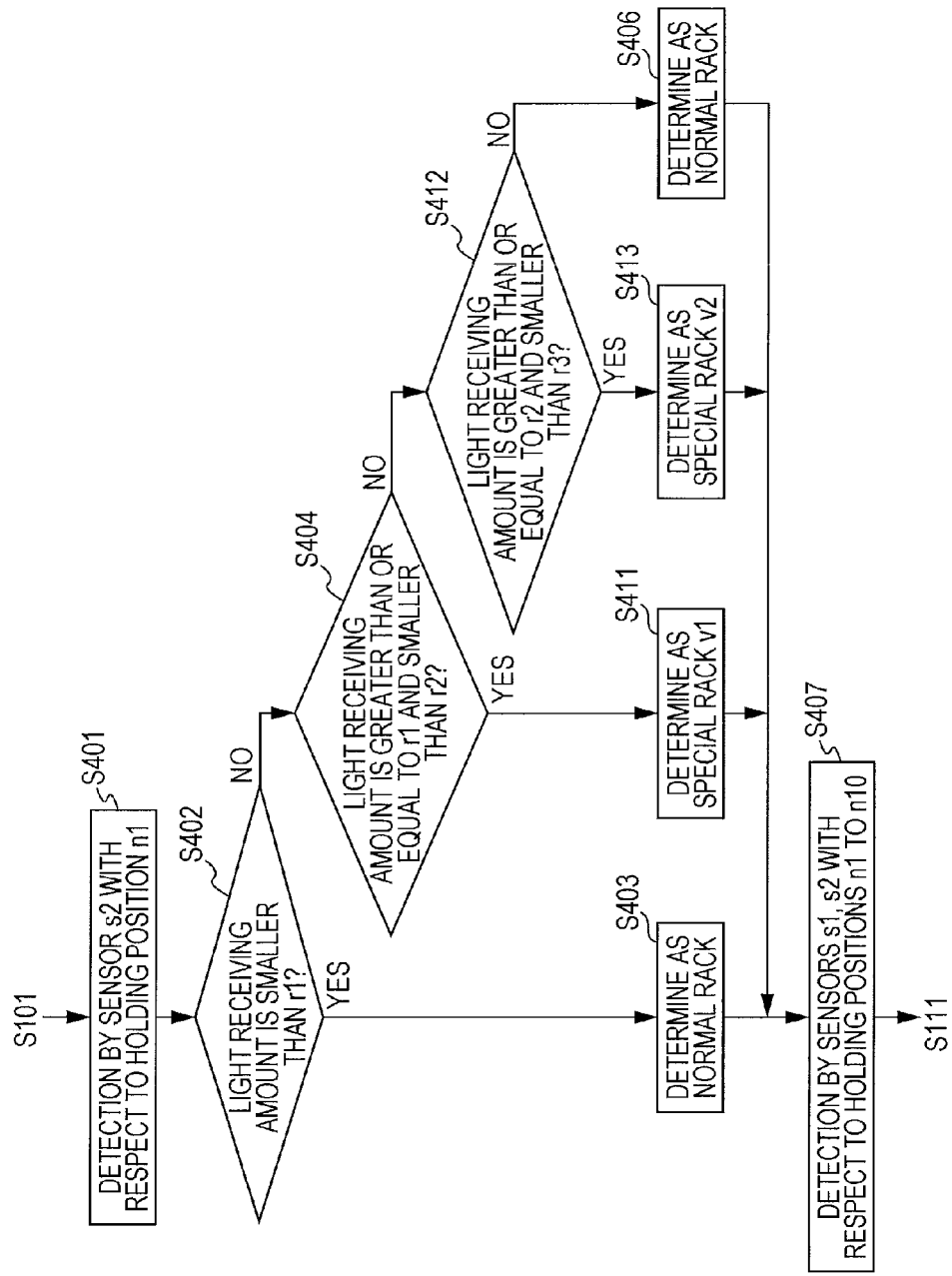

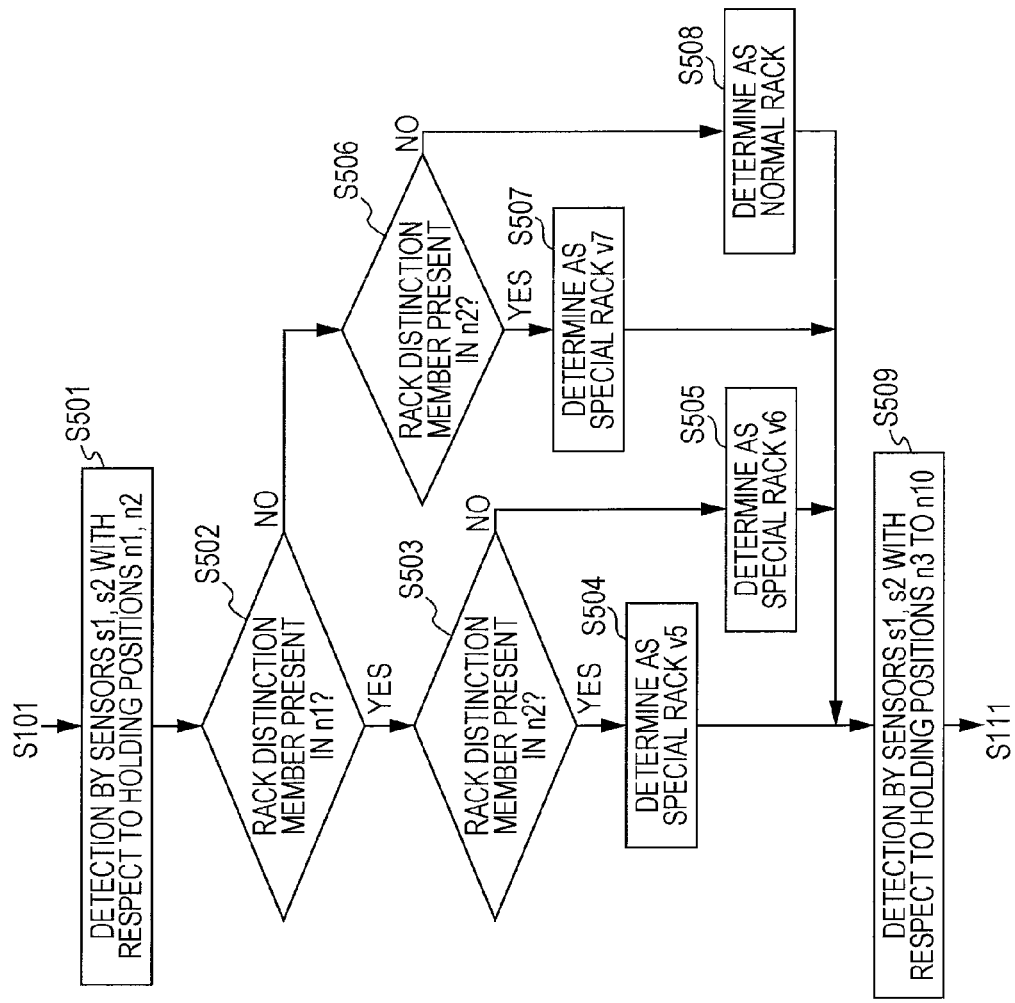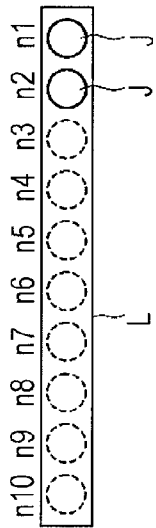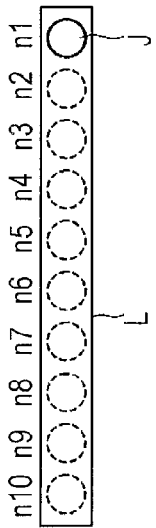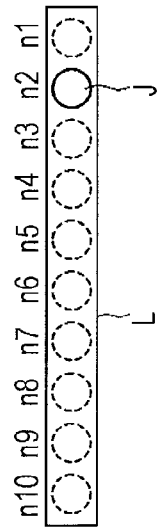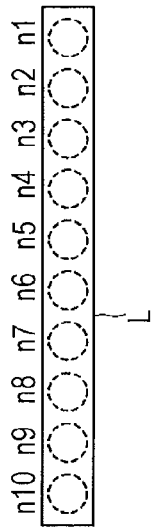

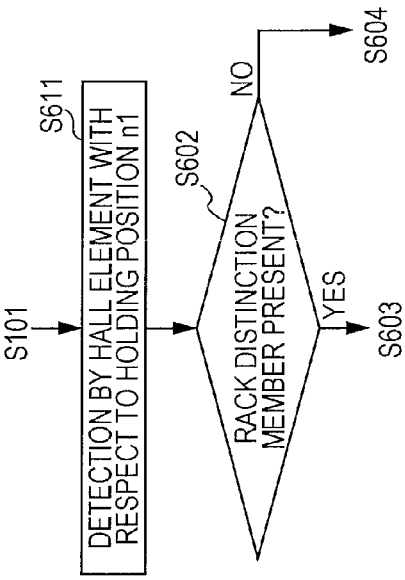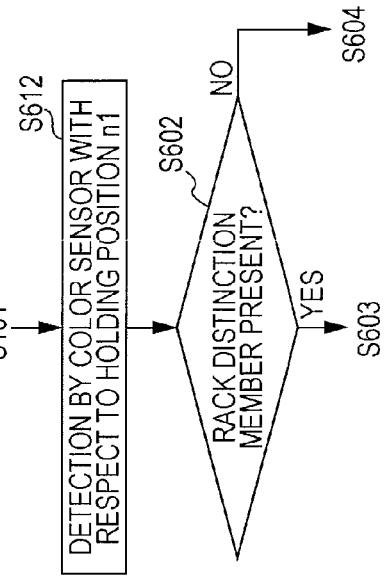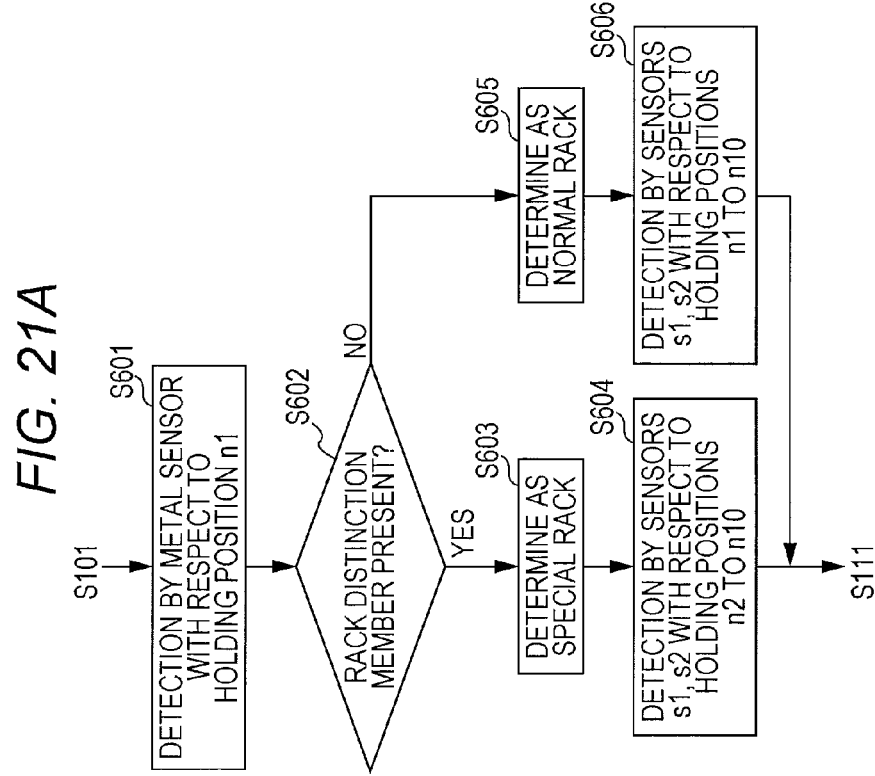

SAMPLE PROCESSING APPARATUS, SAMPLE RACK SET, AND SAMPLE PROCESSING METHOD

RELATED APPLICATIONS

This application claims priority under 35 U.S.C. §119 to Japanese Patent Application No. 2013-045818 filed on Mar. 7, 2013, the entire content of which is hereby incorporated by reference.

FIELD OF THE INVENTION

The present invention relates to a sample processing apparatus for performing processing on a sample container, and a sample rack set used in the sample processing apparatus.

BACKGROUND OF THE INVENTION

A sample processing apparatus that aspirates a sample in a sample container held in a sample rack to perform sample processing is known. The sample container may be of various types having different shapes such as inner diameters, outer shapes, lengths, and the like, and thus the aspirating operation and the like need to be changed according to the shape of the sample container when performing the aspirating operation and the like with respect to the sample container in the sample processing apparatus.

In a technique described in U.S. Patent Application Publication No. 200810050279A1, the type of sample container held in the sample rack is distinguished from a barcode attached to the sample rack, and the aspirating operation with respect to the sample container is executed according to the type of distinguished sample container.

However, in a facility that processes a very large number of samples such as a large hospital and an examination center, the barcode attached to the sample rack might get dirty or the barcode may come off from the sample rack while the sample rack is being repeatedly used. Even if the barcode is not peeled off, there is a risk of reading mistake by the barcode reader. In these cases, the barcode attached to the sample rack is not accurately read, and the type of sample container held in the sample rack may not be distinguished.

SUMMARY OF THE INVENTION

The scope of the present invention is defined solely by the appended claims, and is not affected to any degree by the statements within this summary.

A first aspect of the present invention is a sample processing apparatus comprising a transporting section configured to transport a sample rack that is capable of holding a sample container at a plurality of holding positions, a detecting section that is configured to detect presence or absence of a rack distinction member at a holding position of the sample rack, an aspirating section that is configured to aspirate a sample in the sample container, and a control section that is configured to control an aspirating operation of the aspirating section. The control section changes an aspirating operation with respect to the sample container held in the sample rack based on the presence or absence of the rack distinction member at the holding position of the sample rack.

A second aspect of the present invention is a sample rack set comprising a rack main body capable of holding a sample container at a plurality of holding positions, and a rack distinction member capable of being installed at a holding position of the rack main body.

A third aspect of the present invention is a sample processing method comprising transporting a sample rack capable of holding a sample container at a plurality of holding positions, distinguishing presence or absence of a rack distinction member at the holding position of the sample rack, and aspirating a sample in the sample container. In the aspirating step, an aspirating operation with respect to the sample container held in the sample rack is changed based on a distinction result in the distinguishing step.

BRIEF DESCRIPTION OF THE DRAWINGS

FIG. 1 is a view showing an outer appearance of a blood cell analyzer according to a first embodiment;

FIGS. 2A through 2E are outer appearance views and cross-sectional views of a sample container according to the first embodiment, and views showing a configuration of a rack distinction member;

FIGS. 3A and 3B are outer appearance views and side views of a normal rack according to the first embodiment;

FIGS. 4A and 4B are outer appearance views and side views of a special rack according to the first embodiment;

FIGS. 7A through 7D are views describing a stirring operation and an aspirating operation according to the first embodiment, as well as a conceptual diagram showing a configuration of a processing information table;

FIGS. 11A through 11C are outer appearance views of a normal rack and a special rack according to a second embodiment, and views schematically showing the vicinity of a rack transportation unit;

FIGS. 14A and 14B are conceptual diagrams showing a configuration of a registered information table according to the second embodiment, and a flowchart showing processing by the information processing unit according to a variant;

FIG. 16 is a flowchart showing processing by the information processing unit according to the variant;

FIGS. 17A and 17B are views showing a configuration of a rack distinction member according to the variant and a flowchart showing processing by the information processing unit;

FIGS. 18A through 18C are views showing a configuration of the rack distinction member according to the variant and a flowchart showing processing by the information processing unit;

FIGS. 20A through 20E are views showing a special rack and a normal rack according to the variant, and a flowchart showing processing by the information processing unit; and FIGS. 21A through 21C are flowcharts showing processing by the information processing unit according to the variant.

DETAILED DESCRIPTION OF THE PREFERRED EMBODIMENTS

Figure 5:
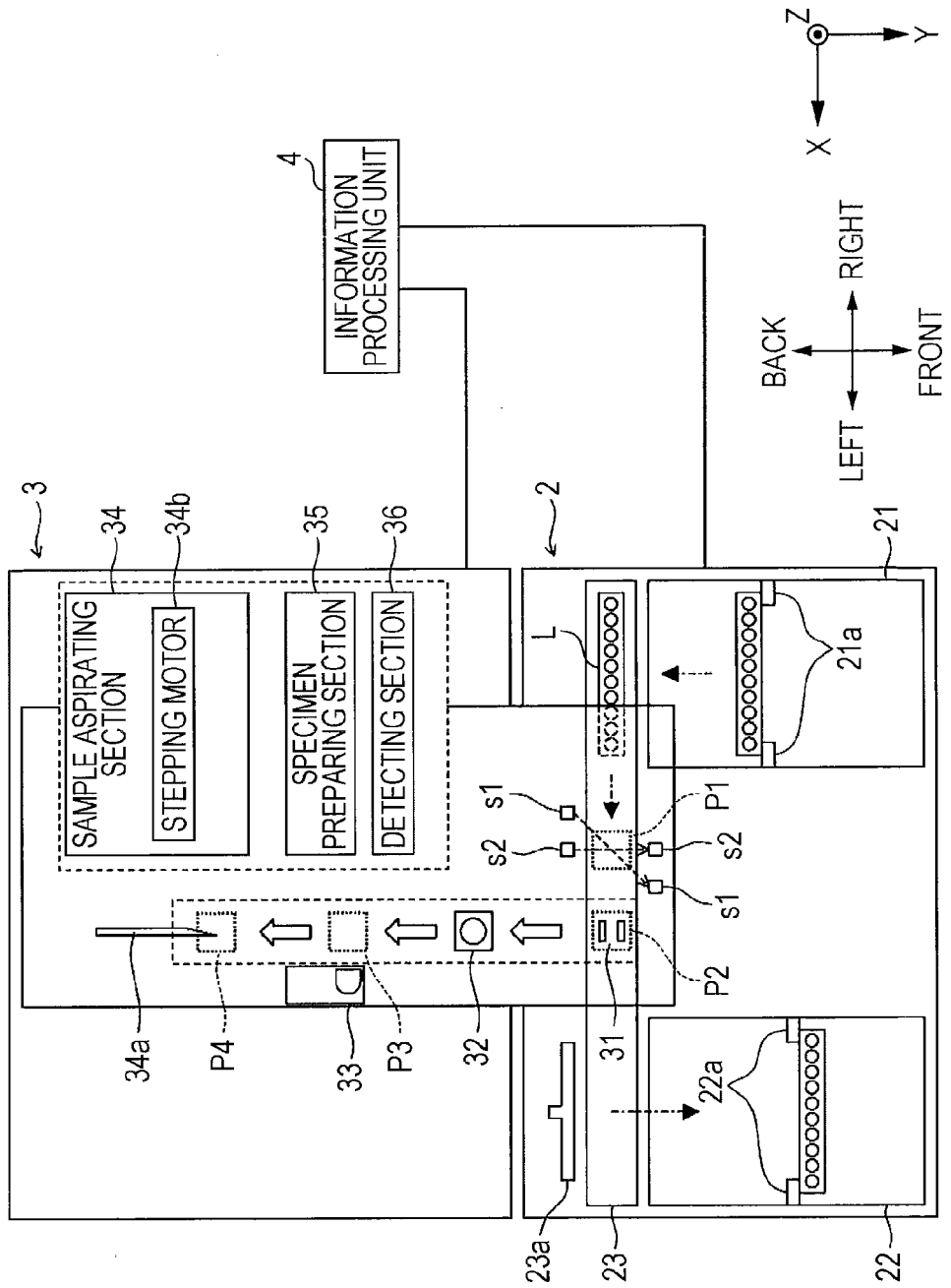
FIG. 5 is a view schematically showing a configuration of a transportation unit and a measurement unit according to the first embodiment.

The preferred embodiments of the present invention will be described hereinafter with reference to the drawings.

In the present embodiment, the present invention is applied to a blood cell analyzer for performing examinations and analysis related to blood.

First Embodiment

FIG. 1 is a view showing an outer appearance of a blood cell analyzer 1 according to the present embodiment. The blood cell analyzer 1 includes a transportation unit 2, a measurement unit 3, and an information processing unit 4.

The transportation unit 2 is arranged on a front side of the measurement unit 3, and includes a right table 21, a left table 22, and a rack transporting section 23 that connects the right table 21 and the left table 22. The right table 21 and the left table 22 can accommodate a plurality of sample racks L. The rack transporting section 23 includes a belt 23b, which extends along an X-axis direction, and transports a sample rack L transported out to the back side (negative direction side in Y-axis) of the right table 21 to the back side of the left table 22 by driving the belt 23b in the X-axis direction.

The sample rack L includes ten holders L1, and can hold a sample container T1 or a sample container T2 by way of the holder L1. The configuration of the sample rack L will be described later with reference to FIGS. 3A and 3B, and FIGS. 4A and 4B. The sample containers T1, T2 contain a blood sample of a whole blood collected from a patient. The shape of the outer appearance of the sample containers T1, T2 is substantially the same, but the internal structure is different. The configuration of the sample containers T1, T2 will be described later with reference to FIGS. 2A to 2D.

When starting the measurement of the sample contained in the sample container T1, the user sets only the sample container T1 in the sample rack L for holding, and places the sample rack L on the right table 21. When starting the measurement of the sample contained in the sample container T2, on the other hand, the user sets only the sample container T2 in the sample rack L for holding, and places the sample rack L on the right table 21. Subsequently, the sample rack L set on the right table 21 is sequentially transported by the transportation unit 2, and the sample is supplied to the measurement unit 3. After the process is completed, the sample rack L is accommodated in the left table 22. The configurations of the transportation unit 2 and the measurement unit 3 will be described later with reference to FIG. 5.

The information processing unit 4 includes a display section 41 and an input section 42, and is communicably connected to the transportation unit 2 and the measurement unit 3. The information processing unit 4 controls each section of the transportation unit 2 and the measurement unit 3, and receives signals detected by a sensor and the like arranged in the transportation unit 2 and the measurement unit 3. The information processing unit 4 also performs analysis based on the signal received from the measurement unit 3, and detects blood cells contained in a measurement specimen. The information processing unit 4 displays the analysis result on the display section 41.

FIGS. 2A and 2B are an outer appearance view and a cross-sectional view, respectively, of the sample container T1.

The sample container T1 includes a body portion T11, a lid portion T12, and a barcode label T13. The body portion T11 is a tubular container made of glass or synthetic resin having translucency, where an opening is formed at the upper end and a bottom surface T11a is formed at the lower end of the inside. The body portion T11 accommodates the sample, and the opening at the upper end is sealed by the lid portion T12. The lid portion T12 is configured such that a piercer 34a (see FIG. 5) can pass through. The barcode label T13 is printed with a barcode including a sample ID. The barcode label T13 is attached to the side surface of the body portion T11.

FIGS. 2C and 2D are an outer appearance view and a cross-sectional view, respectively, of the sample container T2. The sample container T2 is a sample container for accommodating the sample container T1 and a sample of lesser volume than the sample container T1.

The sample container T2 includes a body portion T21, a lid portion T22, and a barcode label T23, and has substantially the same height as the sample container T1. The body portion T21 is a tubular container made of glass or synthetic resin having translucency, where an opening is formed at the upper end and a bottom surface T21a is formed at the middle stage of the inside. Similar to the body portion T11 of the sample container T1, the body portion T21 accommodates the sample, and the opening at the upper end is sealed by the lid portion T22. The lid portion T22 and the barcode label T23 have substantially the same configuration as the lid portion T12 and the barcode label T13 of the sample container T1.

The sample rack L for holding only the sample container T1 is referred to as "normal rack" and the sample rack L for holding only the sample container T2 is referred to as "special rack". The normal rack and the special rack differ in whether or not a rack distinction member J shown in FIG. 2(e) is installed at the leading holder L1. The normal rack and the special rack will be hereinafter described in order.

FIGS. 3A and 3B are an outer appearance view and a side view, respectively, of the normal rack.

The sample rack L is formed with ten holders L1 so that ten sample containers T1, T2 can be perpendicularly held. The position of each holder L1 is hereinafter referred to as holding positions n1 to n10 in order toward the negative direction of the X-axis for the sake of convenience. A bottom surface L11 is formed at the lower end of the holder L1, and openings L12, L13 are respectively formed on the negative direction side of the Y-axis and the positive direction side of the Y-axis of the holder L1.

A plate member L2 is installed on the bottom surface L11. The plate member L2 perpendicularly supports the lower end of the body portion T11 of the sample container T1. Furthermore, ten recesses L14 are formed to correspond to the bottom surface L11 on the surface in the negative direction side of the Z-axis of the sample rack L. The plate member L2 is installed on the bottom surface L11 by passing a tube portion L21 formed at the lower surface of the plate member L2 to a hole passing through the bottom surface L11 and the recess L14.

Thus, the normal rack is configured without the rack distinction member J installed at the holding position n1 in the sample rack L. When starting the measurement of the sample contained in the sample container T1, the user appropriately sets the sample container T1 in the holding positions n1 to n10 of the normal rack. When the sample container T1 is set in the normal rack, the upper end of the sample container T1 is located on the upper side than the upper surface of the sample rack L.

FIGS. 4A and 4B are an outer appearance view and a side view, respectively, of the special rack.

In the special rack, the rack distinction member J is installed at the holding position n1 of the sample rack L. The rack distinction member J has a substantially cylindrical shape. Similar to the sample rack L, the rack distinction member J is made of ABS resin and the like, so that the rack distinction member J and the sample rack L both do not pass light. When installing the rack distinction member J in the sample rack L, the plate member L2 installed at the bottom surface L11 of the holding position n1 is first detached from the normal rack. Then, the rack distinction member J is inserted from the upper side to the holder L1 at the holding position n1, and the lower end of the rack distinction member J is fixed to the bottom surface L1 by a screw J1 through the hole passing through the bottom surface L11 and the recess L14. When the rack distinction member J is installed in the holder L1 at the holding position n1 in such manner, the upper surface of the rack distinction member J is located at substantially the same height as the upper surface of the sample rack L, and the rack distinction member J is configured not to jump out from the upper surface of the sample rack L, as shown in FIGS. 4A and 4B. The rack distinction member J may not necessarily be fixed by the screw J1.

Thus, the special rack is configured with the rack distinction member J installed at the holding position n1 in the sample rack L. When starting the measurement of the sample contained in the sample container T2, the user appropriately sets the sample container T2 in the holding positions n2 to n10 of the special rack. When the sample container T2 is set in the special rack, the upper end of the sample container T2 is located on the upper side than the upper surface of the sample rack L.

FIG. 5 is a view schematically showing a configuration of the transportation unit 2 and the measurement unit 3.

The rack transporting section 23 includes transmissive sensors s1, s2 including a light emitting portion and a light receiving portion, a belt 23b (see FIG. 1), and a rack push-out mechanism 23a for transporting the sample rack L forward. The right table 21 includes a rack push-out mechanism 21a for transporting the sample rack L backward, and the left table 22 includes a rack push-out mechanism 22a for transporting the sample rack L forward. The measurement unit 3 includes a gripping section 31, a sample container setting section 32, a barcode unit 33, a sample aspirating section 34, a specimen preparing section 35, and a detecting section 36. The sample aspirating section 34 includes a piercer 34a for aspirating the samples in the sample containers T1, T2, and a stepping motor 34b for driving the piercer 34a in the up and down direction.

The sample rack L is transported in the left direction by the rack transporting section 23. After the holder L1 of the sample rack L is positioned at a predetermined position P1 on the rack transporting section 23, detection by the sensors s1, s2 is carried out. The light emitting portion and the light receiving portion of the sensor s1 are installed on the right back side and the left front side of the position P1, and the light emitting portion and the light receiving portion of the sensor s2 are installed on the back side and the front side of the position P1. Whether or not the sample containers T1, T2 are held at the holding position positioned at the position P1 is detected by the sensor s1, and whether or not the sample is contained in the sample container T1 held at the holding position positioned at the position P1 is detected by the sensor s2.

Figure 6A:
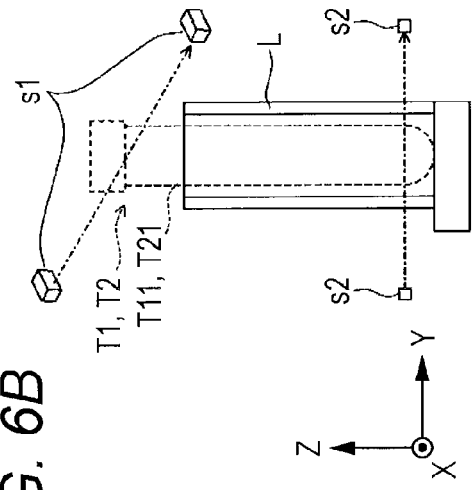
FIGS. 6A through 6F are side views of a sensor and side views of the sample rack according to the first embodiment.
Figure 6B:
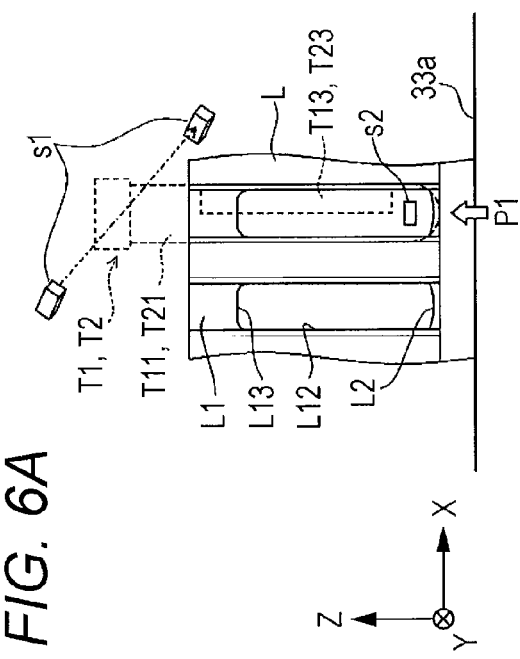

FIGS. 6A and 6B are side views of when the sensors s1, s2 are seen from the positive direction in the Y-axis and the negative direction in the X-axis, respectively. In FIGS. 6A and 6B, a state in which the holding position of the sample rack L is positioned at the position P1 is shown, where the sample containers T1, T2 held at the holding position positioned at the position P1 are shown with a broken line.

The sensor s1 is installed in the transportation unit 2 so that the detection position is positioned at the upper side of the holder L1 positioned at the position P1. The sensor s2 is installed in the transportation unit 2 so that the detection position is positioned at the upper side than the bottom surface 11a of the sample container T1 and the plate member L2 positioned at the position P1 and the lower side than the barcode labels T13, T23. The light emitting portion and the light receiving portion of the sensor s2 can directly face each other by way of the openings L12, L13 of the holder L1 even if the holder L1 is positioned at the position P1. Thus, the sensor s2 detects the presence or absence of the detection target at a height different from the sensor s1.

When the light emitted from the light emitting portion of the sensor s1 is received by the light receiving portion of the sensor s1, the detection result of the sensor s1 becomes "sample container absent". When the light emitted from the light emitting portion of the sensor s1 is not received by the light receiving portion of the sensor s1, the detection result of the sensor s1 becomes "sample container present". When the light of greater than or equal to a predetermined value of the light emitted from the light emitting portion of the sensor s2 is received by the light receiving portion of the sensor s2, the detection result of the sensor s2 becomes "sample absent". Since the sensor s2 is installed on the upper side than the bottom surface T11a of the sample container T1, the detection result of the sensor s2 becomes "no sample" even if the sample container T1 does not contain a predetermined amount of sample necessary for measurement and contains a slight amount of sample. When the light of smaller than a predetermined value of the light emitted from the light emitting portion of the sensor s2 is not received by the light receiving portion of the sensor s2, the detection result of the sensor s2 becomes "sample present".

Figure 6C:
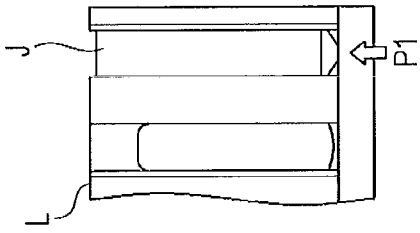

For example, as shown in FIG. 6C, when the sample container T1 containing a predetermined amount of sample is positioned at the holding position positioned at the position P1, the detection result of the sensor s1 becomes "sample container present". Since only the light of smaller than the predetermined value enters the light receiving portion of the sensor s2, the detection result of the sensor s2 becomes "sample present".

Figure 6D:
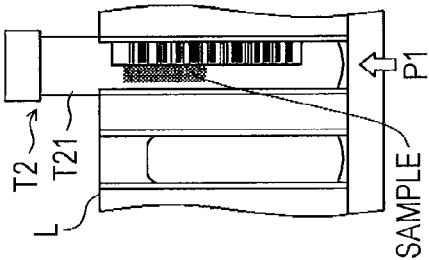

Furthermore, as shown in FIG. 6D, when the sample container T1 that does not contain the sample or that does not contain a predetermined amount of sample is positioned at the holding position positioned at the position P1, the detection result of the sensor s1 becomes "sample container present". Furthermore, since the light of greater than or equal to a predetermined value enters the light receiving portion of the sensor s2, the detection result of the sensor s2 becomes "sample absent".

Figure 6E:
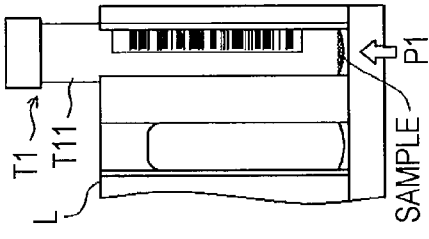

For example, as shown in FIG. 6E, when the sample container T2 containing a sample is positioned at the holding position positioned at the position P1, the detection result of the sensor s1 becomes "sample container present". Furthermore, since the light of greater than or equal to a predetermined value enters the light receiving portion of the sensor s2, the detection result of the sensor s2 becomes "sample absent". The bottom surface T21a of the sample container T2 is on the upper side than the sensor s2, so that the detection result of the sensor s2 is always "sample absent" even if the sample container T2 contains a sample.

Figure 6F:
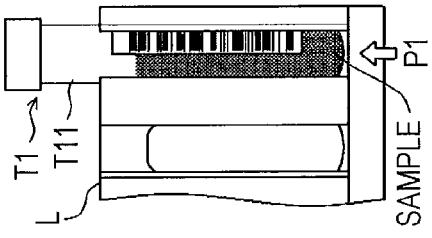

Moreover, as shown in FIG. 6F, when the rack distinction member J is installed at the holding position positioned at the position P1, the detection result of the sensor s1 becomes "sample container absent". Since the light does not enter the light receiving portion of the sensor s2, the detection result of the sensor s2 becomes "sample present". If none of the sample containers T1, T2 and the rack distinction member J is installed at the holding position positioned at the position P1, the detection result of the sensor s1 becomes "sample container absent". Furthermore, since the light of greater than or equal to a predetermined value enters the light receiving portion of the sensor s2, the detection result of the sensor s2 becomes "sample absent".

Returning back to FIG. 5, when the detection by the sensors s1, s2 is terminated at the position P1, the sample containers T1, T2 held in the sample rack L are then positioned at a predetermined position P2 on the rack transporting section 23. The sample containers T1, T2 positioned at the position P2 is gripped by the gripping section 31, and pulled out upward from the sample rack L. The gripping section 31 over-turns the sample containers T1, T2 by a predetermined number of times to stir the sample in the sample containers T1, T2. The stirring operation with respect to the sample containers T1, T2 will be described later with reference to FIG. 7A.

The sample containers T1, T2 in which the stirring operation is terminated are set in the sample container setting section 32 positioned at the position P2 by the gripping section 31. The sample containers T1, T2 are then transported to the position P3 by the sample container setting section 32. After the sample containers T1, T2 are positioned at the position P3, the sample ID is read from the barcode labels T13, T23 attached to the sample containers T1, T2 by the barcode unit 33 installed in the vicinity of the position P3. The sample containers T1, T2 are then transported to the position P4 by the sample container setting section 32. After the sample containers T1, T2 are positioned at the position P4, a predetermined amount of sample is aspirated from the sample containers T1, T2 through the piercer 34a by the sample aspirating section 34. The aspirating operation with respect to the sample containers T1, T2 will be described later with reference to FIGS. 7B and 7C.

After the aspiration of the sample is terminated, the sample containers T1, T2 are transported forward by the sample container setting section 32, and returned to the holding position of the original sample rack L by the gripping section 31. The sample rack L is transported in the left direction by the rack transporting section 23, transported forward by the rack push-out mechanisms 23a, 22a, and collected by the left table 22. The sample aspirated through the piercer 34a is discharged to the reagent preparing section 35 by the sample aspirating section 34. The specimen preparing section 35 mixes the sample and the reagent, warms the mixed solution, prepares the measurement specimen, and supplies the prepared measurement specimen to the detecting section 36. The detecting section 36 acquires various signals by irradiating the measurement specimen with laser light, and transmits the acquired signals to the information processing unit 4.

FIG. 7A is a view showing the stirring operation with respect to the sample containers T1, T2.

The gripping section 31 includes a pair of hand members 31a, and a shaft 31b for supporting the hand members 31a. When the sample container T1, T2 is positioned at the position P2, the gripping section 31 is driven in the negative direction of Z-axis, and the lid portion T12, T22 of the sample container T1, T2 is sandwiched from the Y-axis direction by the hand members 31a. The gripping section 31 is then driven in the positive direction of Z-axis, and the sample containers T1, T2 are taken out from the sample rack L. When the shaft 31b is rotated with the Y-axis as the center in such state, the sample container T1, T2 is turned over by a predetermined number of times with the shaft 31b as the center in a range of an angle indicated with a broken line, as shown in FIG. 7A. The sample in the sample container T1, T2 is thereby stirred.

In this case, number of times fn2 for turning over the sample container T1 is set to be greater than number of times fn1 for rotating the sample container T1. This is because the space region capable of accommodating the sample in the sample container T2 is small compared to the space region capable of accommodating the sample in the sample container T1, as shown in FIGS. 2B and 2D. Thus, the number of turnovers necessary for appropriately stirring the sample in the sample container T2 is greater than the number of turnovers necessary for appropriately stirring the sample in the sample container T1.

FIGS. 7B and 7C are views showing the aspirating operation with respect to the sample containers T1, T2, respectively.

With reference to FIG. 7B, when the sample container T1 is positioned at the position P4, the position in the up and down direction (Z-axis direction) of the piercer 34a is adjusted such that the distal end (lower end portion) of the piercer 34a is positioned at the origin. Then, the piercer 34a is driven in the downward direction so that the distal end of the piercer 34a is positioned at the bottom surface T11a, as shown with a solid line arrow. The sample in the sample container T1 is then aspirated by the piercer 34a.

In this case, the number of pulses applied to the stepping motor 34b for driving the piercer 34a in the downward direction is pn1, which is necessary for lowering the piercer 34a from the origin to the bottom surface T11a, as shown with a broken line arrow. The torque of the stepping motor 34b, that is, the force for driving the piercer 34a in the downward direction is tr1. The distal end of the piercer 34a is thereby passed through the lid portion T12 and positioned on the bottom surface T11a.

With reference to FIG. 7C, when the sample container T2 is positioned at the position P4, the position in the up and down direction of the piercer 34a is adjusted such that the distal end of the piercer 34a is positioned at the origin, similar to the case of the sample container T1. Then, the piercer 34a is driven in the downward direction so that the distal end of the piercer 34a is positioned at the bottom surface T21a, as shown with a solid line arrow. The sample in the sample container T2 is then aspirated by the piercer 34a.

In this case, the number of pulses applied to the stepping motor 34b is pn2, which is greater than the number of pulses necessary for lowering the piercer 34a from the origin to the bottom surface T21a, as shown with a broken line arrow. The torque of the stepping motor 34b is tr2, which is smaller than tr1 for the case of the sample container T1 and at which the piercer 34a can pass through the lid portion T22. Accordingly, the distal end of the piercer 34a can be passed through the lid portion T22 and the bottom surface T21a and the distal end of the piercer 34a are avoided from being damaged even after the piercer 34a is brought into contact with the bottom surface T21a. After the application of the number of pulses pn2 is finished, the distal end of the piercer 34a is positioned on the bottom surface T11a.

Figure 8:
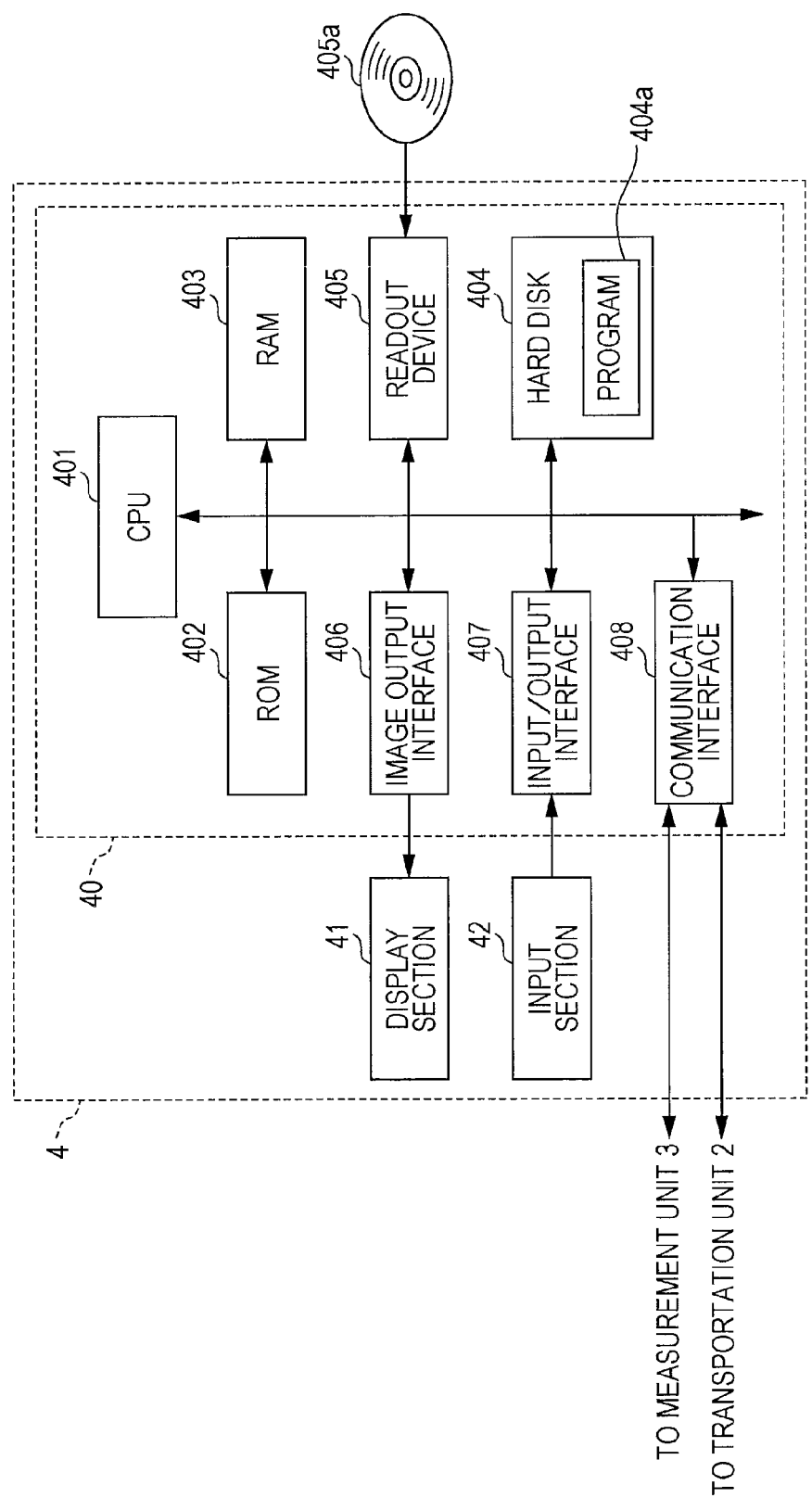
FIG. 8 is a view showing a configuration of an information processing unit according to the first embodiment.

FIG. 7D is a conceptual diagram showing a configuration of a processing information table stored in the hard disk 404 (see FIG. 8).

When performing the stirring operation on the sample container T1, T2, the information processing unit 4 acquires the corresponding number of turnovers with reference to the processing information table, and controls the stirring operation by the gripping section 31 based on the acquired number of turnovers. When performing the aspirating operation on the sample container T1, T2, the information processing unit 4 acquires the corresponding number of pulses and torque with reference to the processing information table, and controls the aspirating operation by the sample aspirating section 34 based on the acquired number of pulses and torque.

FIG. 8 is a view showing a configuration of the information processing unit 4.

The information processing unit 4 includes a personal computer, and is configured by a main body 40, the display section 41, and the input section 42. The main body 40 includes a CPU 401, a ROM 402, a RAM 403, a hard disk 404, a readout device 405, an image output interface 406, an input/output interface 407, and a communication interface 408.

The CPU 401 executes computer programs stored in the ROM 402 and the computer programs loaded in the RAM 403. The RAM 403 is used to read out the computer programs recorded on the ROM 402 and the hard disc 404. In executing the computer programs, the RAM 403 is also used as a work region of the CPU 401.

The hard disk 404 is stored with the operating system, the computer programs to be executed by the CPU 401, and the data used in the execution of the computer programs. Furthermore, the hard disk 404 is stored with a program 404a for controlling each unit of the blood cell analyzer 1, and the processing information table shown in FIG. 7D.

The readout device 405 is configured by a CD drive, DVD drive, and the like, and can read out the computer programs and data recorded on a recording medium 405a. If the program 404a is recorded on the recording medium 405a, the program 404a read out from the recording medium 405a by the readout device 405 is stored in the hard disk 404.

The image output interface 406 outputs a video signal corresponding to the image data to the display section 41, and the display section 41 displays the image based on the video signal output from the image output interface 406. The user inputs an instruction through the input section 42, and the input/output interface 407 receives the signal input through the input section 42. The communication interface 408 is connected to the transportation unit 2 and the measurement unit 3, and the CPU 401 performs transmission/reception of instruction signals and data with such devices through the communication interface 408.

Figure 9:
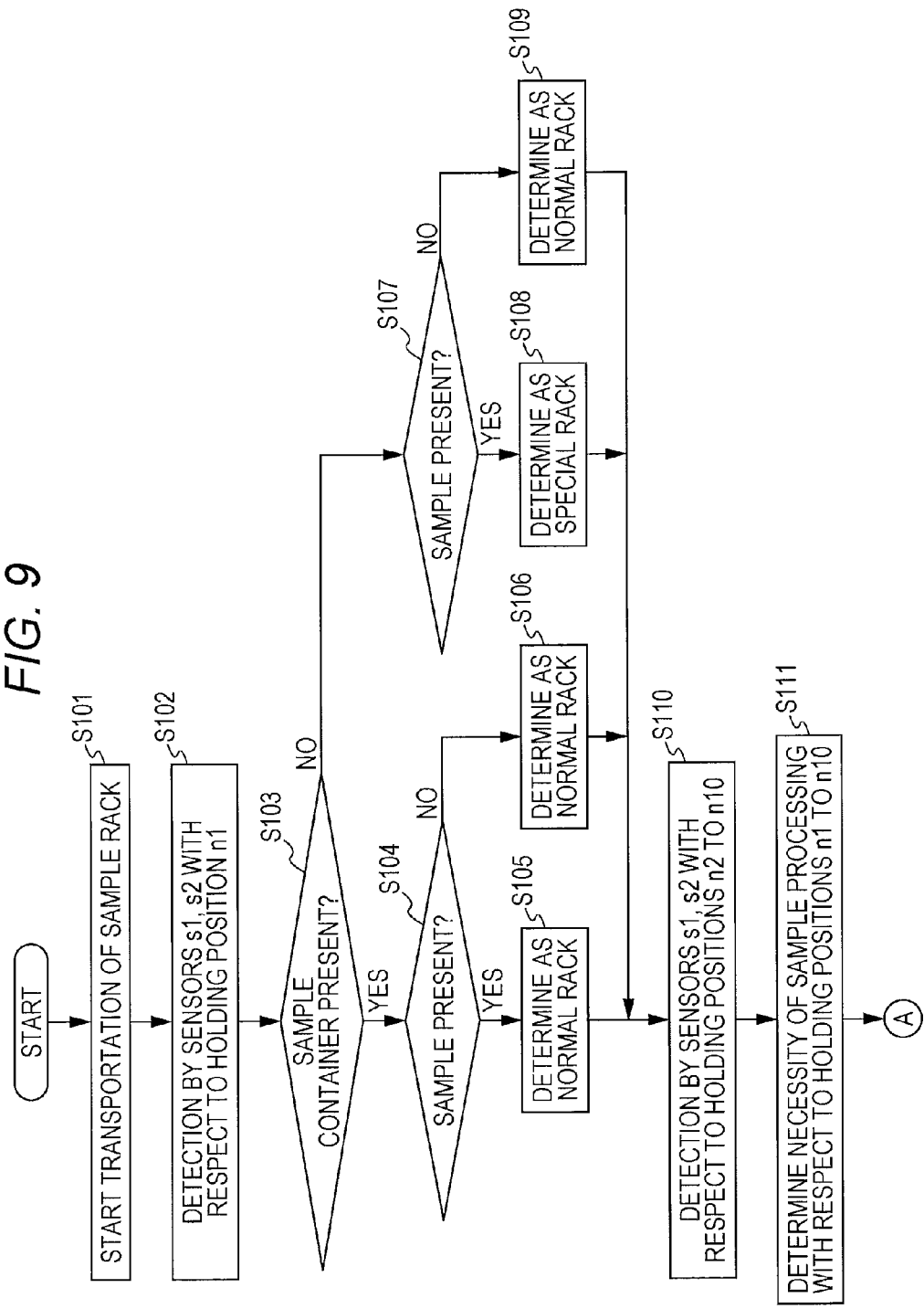
FIG. 9 is a flowchart showing processing by the information processing unit according to the first embodiment.
Figure 10:
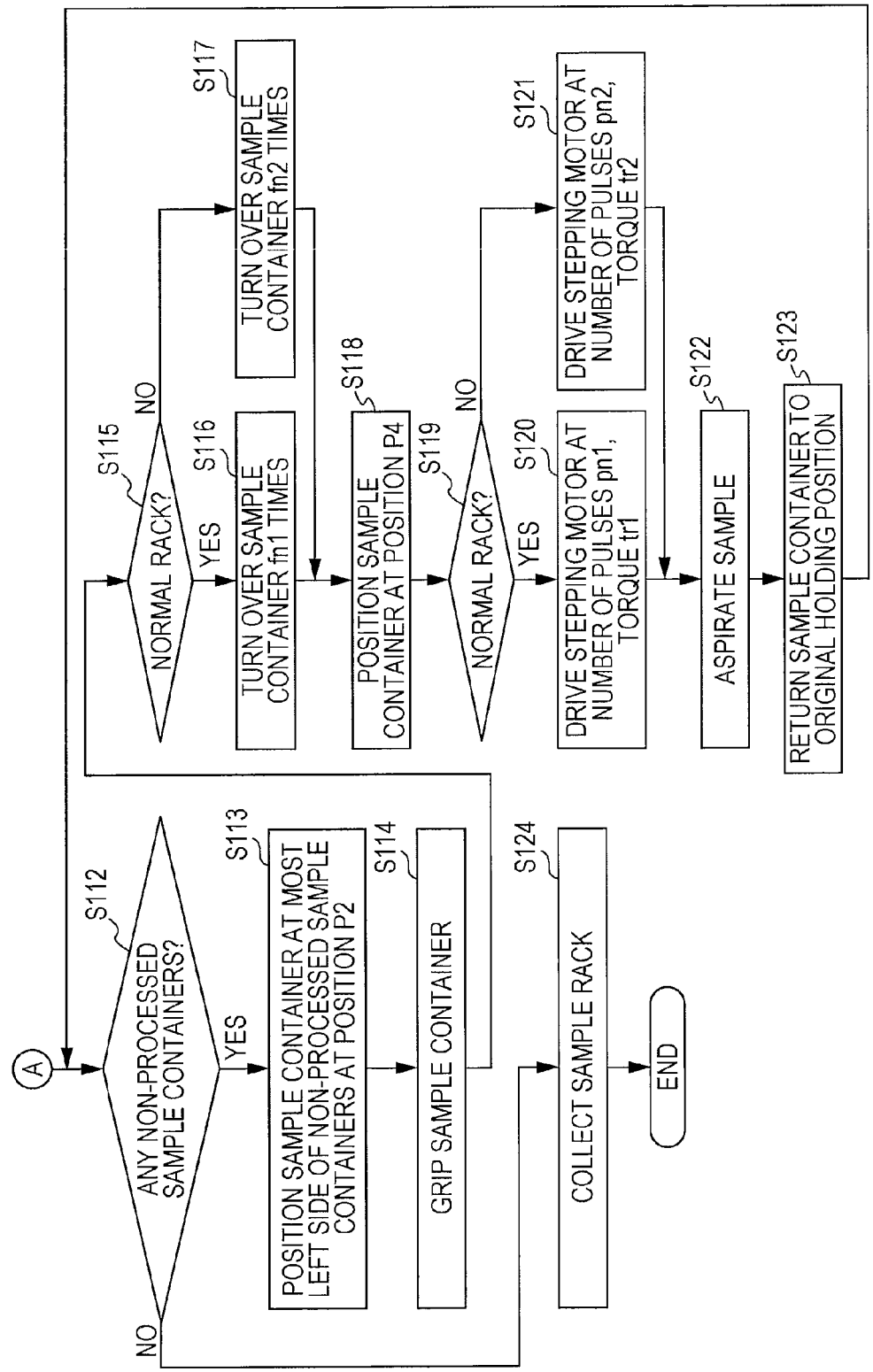
FIG. 10 is a flowchart showing processing by the information processing unit according to the first embodiment.

FIGS. 9 and 10 are flowcharts showing processing by the information processing unit 4. The processing of FIGS. 9 and 10 is started when the sample rack L is placed on the right table 21.

With reference to FIG. 9, when the sample rack L is placed on the right table 21, the CPU 401 of the information processing unit 4 starts the transportation of the sample rack L placed on the right table 21 (S101). The sample rack L is thereby transported from the right table 21 to the rack transporting section 23, and the holding position n1 is positioned at the position P1. The CPU 401 then performs detection by the sensors s1, s2, as described above, with respect to the holding position n1 positioned at the position P1 (S102). The presence/absence of the detection target is thereby detected.

If the detection result of the sensor s1 is "sample container present" (S103: YES) and the detection result of the sensor s2 is "sample present" (S104: YES), the CPU 401 determines the relevant sample rack L as the sample rack L that holds only the sample container T1, that is, the normal rack (S105). This case corresponds to when the sample container T1, in which a predetermined amount of sample necessary for measurement is accommodated, is held at the holding position n1 positioned at the position P1, as shown in FIG. 6C.

If the detection result of the sensor s1 is "sample container present" (S103: YES) and the detection result of the sensor s2 is "sample absent" (S104: NO), the CPU 401 determines the relevant sample rack L as the normal rack (S106). This case corresponds to when the sample container T1, in which a predetermined amount of sample necessary for measurement is not accommodated, is held at the holding position n1 positioned at the position P1, as shown in FIG. 6D.

If the detection result of the sensor s1 is "sample container absent" (S103: NO) and the detection result of the sensor s2 is "sample present" (S107: YES), the CPU 401 determines the relevant sample rack L as the sample rack L that holds only the sample container T2, that is, the special rack (S108). This case corresponds to when the rack distinction member J is held at the holding position n1 positioned at the position P1, as shown in FIG. 6F.

Furthermore, if the detection result of the sensor s1 is "sample container absent" (S103: NO) and the detection result of the sensor s2 is "sample absent" (S107: NO), the CPU 401 determines the relevant sample rack L as the normal rack (S109). This case corresponds to when none of the sample containers T1, T2 nor the rack distinction member J is held at the holding position n1 positioned at the position P1.

When starting the measurement on the sample container T1, T2, the user causes only the sample container T1 to be held in the sample rack L and only the sample container T2 to be held in the sample rack L. Thus, the CPU 401 can distinguish the type of sample container held in the sample rack L when the type of sample rack L is determined as described above. In other words, the CPU 401 distinguishes that the sample containers being held are all sample containers T1 when determined that the sample rack L is the normal rack, and distinguishes that the sample containers being held are all sample containers T2 when determined that the sample rack L is the special rack.

The CPU 401 then transports the sample rack L in the left direction, positions the holding positions n2 to n10 at the position P1 in order, and performs the detection by the sensors s1, s2 with respect to the holding positions n2 to n10 (S110). The presence/absence of the detection target is thereby detected with respect to the holding positions n2 to n10.

The CPU 401 then determines the necessity of sample processing with respect to the holding positions n1 to n10 based on the detection results of the sensors s1, s2 in S102 and S110 (S111). Specifically, when determined that the sample rack L is the normal rack in S105, S106, S109, determination is made that the sample processing is necessary with respect to the holding position where the detection result of the sensor s1 is "sample container present" and the detection result of the sensor s2 is "sample present". When determined that the sample rack L is the special rack in S108, determination is made that the sample processing is necessary with respect to the holding position where the detection result of the sensor s1 is "sample container present".

With reference to FIG. 10, the CPU 401 determines whether or not a non-processed sample container exists in the sample rack L (S112). In other words, whether or not the stirring operation and the aspirating operation are performed on all the sample containers held at the holding positions determined that the sample processing is necessary in S111 in the sample rack L.

If the non-processed sample container exists in the sample rack L (S112: YES), the CPU 401 positions the sample container on the most left side, among the non-processed sample containers held in the relevant sample rack L, at the position P2 (S113). The CPU 401 grips the relevant sample container with the gripping section 31 (S114). Then, if the sample rack L is the normal rack (S115: YES), the CPU 401 references the processing information table to acquire the number of turnovers fn1 of the sample container T1, drives the gripping section 31 and turns over the sample container T1 by the acquired number of turnovers (S116). Then, if the sample rack L is the special rack (S115: NO), the CPU 401 acquires the number of turnovers fn2 of the sample container T2 in the processing information table, drives the gripping section 31 and turns over the sample container T2 by the acquired number of turnovers (S117).

The CPU 401 then sets the sample container gripped by the gripping section 31 in the sample container setting section 32, reads the sample ID from the barcode labels T13, T23 with the barcode unit 33, and positions the sample container at the position P4 (S118). If the sample rack L is the normal rack (S119: YES), the CPU 401 positions the piercer 34a at the origin, and then references the processing information table to acquire the number of pulses pn1 and the torque tr1 of the sample container T1, and drives the stepping motor 34b with the acquired number of pulses and torque (S120). The distal end of the piercer 34a is thereby positioned on the bottom surface T11a. If the sample rack L is the special rack (S119: NO), the CPU 401 positions the piercer 34a at the origin, and then references the processing information table to acquire the number of pulses pn2 and the torque tr2 of the sample container T2, and drives the stepping motor 34b with the acquired number of pulses and torque (S121). The distal end of the piercer 34a is thereby positioned on the bottom surface T21a.

The CPU 401 then drives the sample aspirating section 34 and aspirates the sample in the sample container through the piercer 34a (S122). After the aspirating operation is terminated, the sample container is transported forward by the sample container setting section 32, and returned to the holding position of the original sample rack L by the gripping section 31 (S123). The process then returns to S112, and the processes S113 to S123 are carried out until there are no non-processed sample containers in the sample rack L.

When the non-processed sample container no longer exists in the sample rack L (S112: NO), the CPU 401 transports the sample rack L in the left direction by the rack transporting section 23, and collects the same at the left table 22 (S124). The transportation of the sample rack L and the processes on the sample containers T1, T2 held in the sample rack L are thereby terminated.

According to the present embodiment, whether the sample rack L is the normal rack or the special rack is distinguished based on the presence/absence of the rack distinction member J at the holding position n1 of the sample rack L, and the type of sample container held in the sample rack L is distinguished according to the type of sample rack L. Since the rack distinction member is arranged in the holding position of the sample rack, and is protected by the wall surface of the sample rack L and the like so that wear and the like are less likely to occur, the breakage of the rack distinction member J can be suppressed. Therefore, even if the sample rack L is repeatedly used, the type of sample container can be reliably distinguished as opposed to a case of distinguishing the type of sample container by reading the rack ID from the barcode label attached to the sample rack L. Furthermore, since the type of sample container can be distinguished, the stirring operation and the aspirating operation on the sample container can be appropriately carried out according to the distinguished type of sample container.

Furthermore, according to the present embodiment, when determined that the sample rack L is the normal rack, the stepping motor 34b is driven with the number of pulses pn1 and the torque tr1 in the aspirating operation with respect to the sample container T1 held in the relevant sample rack L. When determined that the sample rack L is the special rack, the stepping motor 34b is driven with the number of pulses pn2 and the torque tr2 in the aspirating operation with respect to the sample container T2 held in the relevant sample rack L. Thus, even if the position of the bottom surface differs as with the sample containers T1, T2, the lowering amount of the piercer 34a can be appropriately controlled according to the distinguished type of sample container. The bottom surface of the sample container and the distal end of the piercer 34a are avoided from being damaged.

According to the present embodiment, when determined that the sample rack L is the normal rack, the number of turnovers is fn1 in the stirring operation with respect to the sample container T1 held in the sample rack L. When determined that the sample rack L is the special rack, the number of turnovers is fn2 in the stirring operation with respect to the sample container T2 held in the sample rack L. Thus, even if the space region that can accommodate the sample differs as in the sample containers T1, T2, the stirring operation by the gripping section 31 can be appropriately controlled according to the distinguished type of sample container. The sample accommodated in the sample containers T1, T2 is thus appropriately stirred.

According to the present embodiment, whether or not the rack distinction member J is installed at the holding position n1 can be detected since the detection by the sensors s1, s2 is carried out on the holding position n1. Furthermore, the necessity of sample processing with respect to the holding positions n1 to n10 can be determined since the detection by the sensors s1, s2 is carried out with respect to each holding position. In other words, the sensors s1, s2 can be used not only for the distinction on the presence/absence of the rack distinction member J but also for the determination on the necessity of sample processing. Thus, separate detection mechanisms do not need to be prepared to perform the distinction on the presence/absence of the rack distinction member J and the determination on the necessity of sample processing, whereby the configuration of the blood cell analyzer 1 can be simplified.

According to the present embodiment, the rack distinction member J is installed at the holding position n1 of the sample rack L. Thus, when the sample rack L is transported in the left direction from the right end of the rack transporting section 23, it is positioned at the position P1 first than the other holding positions n2 to n10, and thus the detection by the sensors s1, s2 can be rapidly carried out. The presence/absence of the rack distinction member J thus can be rapidly distinguished, and the type of sample container can also be rapidly distinguished. Since the sample rack L does not need to be returned in the right direction in the detection of the sensors s1, s2 with respect to the holding positions n2 to n10, the detection with respect to other holding positions also can be rapidly carried out.

According to the present embodiment, the rack distinction member J is fixed at the holding position n1 of the sample rack L with the screw J1. Thus, the trouble for the user to set the rack distinction member J in the sample rack L and having the sample rack L as the special rack in each measurement of the sample container T2 is omitted, and the mistake of forgetting to set the rack distinction member J in the sample rack L can be prevented.

Second Embodiment

In the first embodiment described above, whether the sample rack L is the normal rack or the special rack is distinguished based on the presence/absence of the rack distinction member J at the holding position n1 of the sample rack L. In the present embodiment, the barcode label attached to the sample rack L is simultaneously used to distinguish the type of sample rack L.

FIGS. 11A and 11B are respectively outer appearance views of the normal rack and the special rack of the present embodiment. The normal rack and the special rack of the present embodiment each has a configuration in which the barcode label L3 is attached to the side surface on the negative direction side of the Y-axis with respect to the normal rack and the special rack of the first embodiment. The barcode label L3 is printed with a barcode including a rack ID.

FIG. 11C is a view schematically showing the vicinity of the rack transporting section 23 of the present embodiment. In the present embodiment, the sensor s1 of the first embodiment is omitted, and a barcode unit 50 is installed in the vicinity of the position P1. The barcode unit 50 detects whether or not the sample container is held at the holding position of the sample rack L positioned at the position P1, reads the rack ID from the barcode label L3 of the sample rack L positioned at the position P1, and reads the sample ID from the barcode labels T13, T23 of the sample containers T1, T2 positioned at the position P1.

Figure 12A:
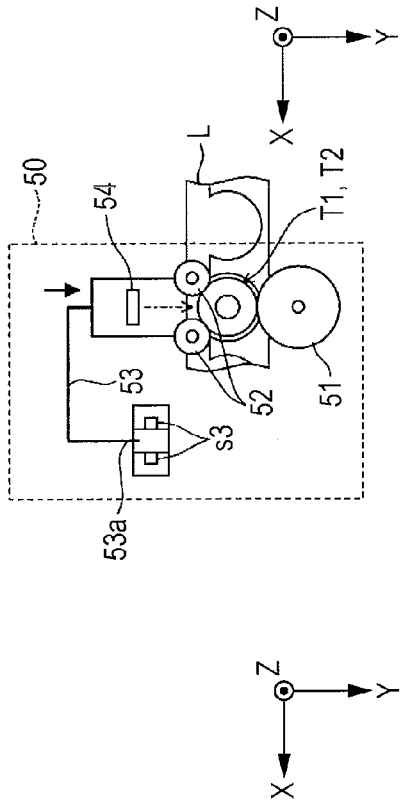
FIGS. 12A through 12D are views showing a configuration of a barcode unit according to the second embodiment.

FIG. 12A is a view schematically showing a configuration of the barcode unit 50. The barcode unit 50 includes a roller 51 for rotating the sample containers T1, T2, a pair of rollers 52, a holder 53 for rotatably supporting the rollers 52, a barcode reader 54, and a transmissive sensor s3 with a light emitting portion and a light receiving portion. The holder 53 is configured to be drivable in the positive direction in the Y-axis from the initial state shown in FIG. 12A. The holder 53 is formed with an end 53a, which end 53a is positioned in the negative direction side in the Y-axis of the sensor s3 at the initial state.

When the position of the holder 53 is at the initial state, the sample rack L is transported in the left direction so that the barcode label L3 is positioned at the position P1 by the rack transporting section 23. Then, as shown in FIG. 12(a), the rack ID is read from the barcode label L3 positioned at the position P1 by the barcode reader 54.

The position of the sample rack L is then returned in the right direction by the rack transporting section 23, and the holding positions n1 to n10 of the sample rack L are positioned at the position P1 in order. When each holding position is positioned at the position P1, the holder 53 is moved in the positive direction in the Y-axis.

Figure 12B:
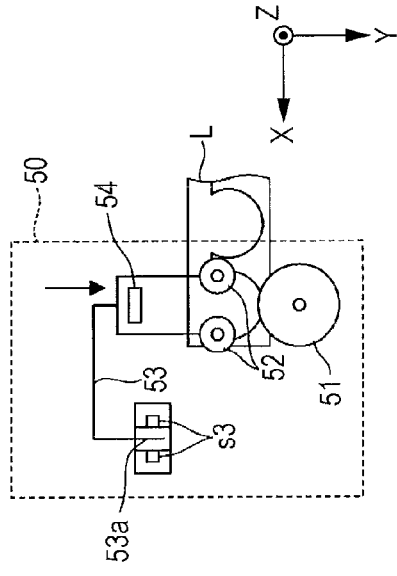
Figure 12C:
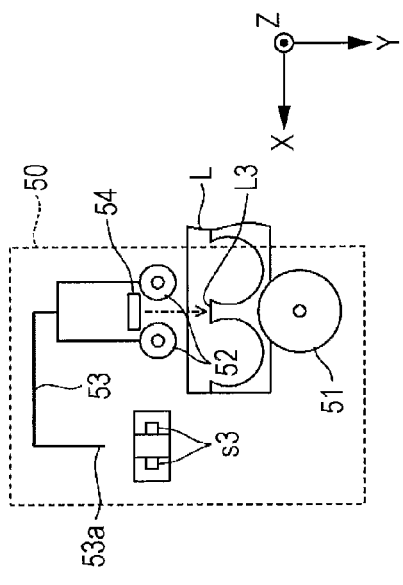
Figure 12D:
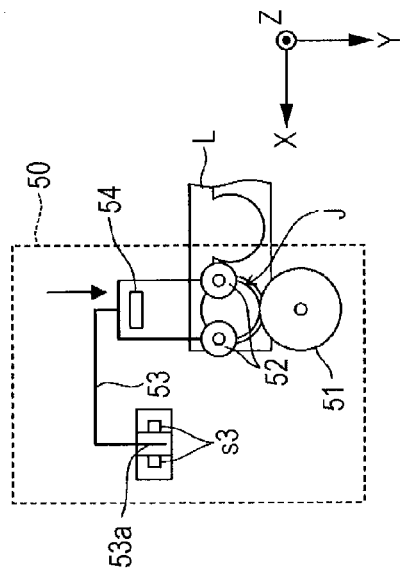

FIGS. 12B to 12D are views each showing a case in which the sample container is held, a case in which the rack distinction member J is held, and a case in which neither the sample container nor the rack distinction member J is held at the holding position positioned at the position P1.

With reference to FIG. 12B, if the sample container is held at the holding position positioned at the position P1, the roller 52 makes contact with the side surface of the sample container. Although the end 53a moves in the positive direction of the Y-axis with the drive of the holder 53, the end does not reach the position of the sensor s3. Thus, when the light emitted from the light emitting portion of the sensor s3 is received by the light receiving portion of the sensor s3, the detection result of the sensor s3 is "sample container present". The sample container T1 is rotated with the Z-axis as the center when the roller 51 is rotated, and the sample ID is read from the barcode labels T13, T23 of the sample container by the barcode reader 54. Similar to the first embodiment described above, the detection of "sample present" or "sample absent" by the sensor s2 is also carried out.

With reference to FIG. 12C, if the rack distinction member J is held at the holding position positioned at the position P1, the roller 52 is moved to the position on the most near side, and the end 53a reaches the position of the sensor s3. Thus, when the light emitted from the light emitting portion of the sensor s3 is not received by the light receiving portion of the sensor s3, the detection result of the sensor s3 is "sample container absent". Similar to the first embodiment described above, the detection by the sensor s2 is also carried out. In this case, the detection result of the sensor s2 is "sample present" since the rack distinction member J is held.

With reference to FIG. 12D, if neither the sample container nor the rack distinction member J is held at the holding position positioned at the position P1, the roller 52 is moved to the position on the most near side, the end 53a reaches the position of the sensor s3, and the detection result of the sensor s3 becomes "sample container absent" similar to FIG. 12C. Similar to the first embodiment described above, the detection by the sensor s2 is also carried out. The detection result of the sensor s2 becomes "sample absent" since neither the sample container nor the rack distinction member J is held.

Therefore, according to the sensor s3 of the present embodiment, the presence/absence of the sample container can be detected with respect to the holding position positioned at the position P1, similar to the sensor s1 of the first embodiment.

Figure 13:
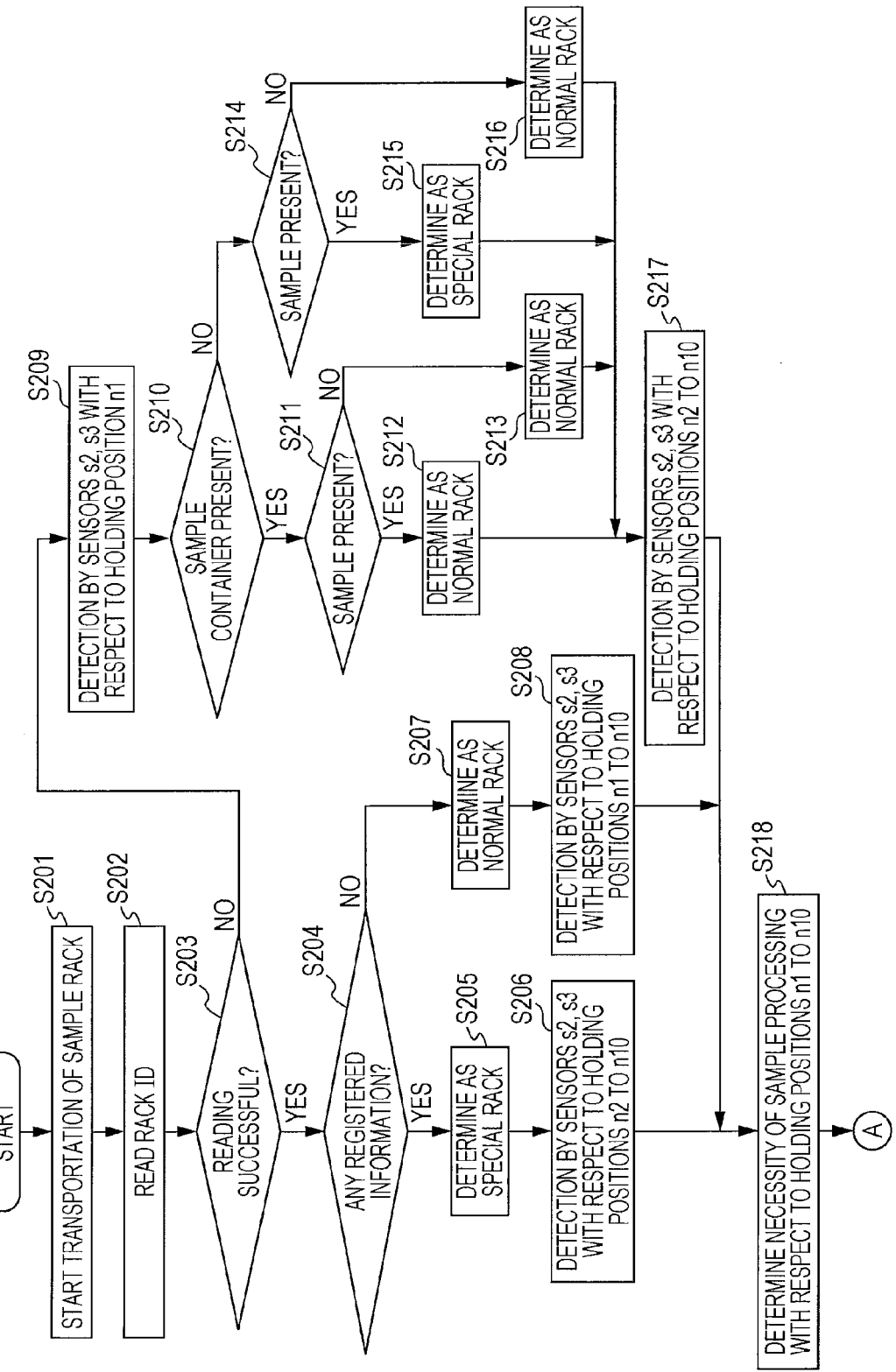
FIG. 13 is a flowchart showing processing by the information processing unit according to the second embodiment.

FIG. 13 is a flowchart showing processing by the information processing unit 4. In the present embodiment, the processing (S201 to S218) of FIG. 13 is carried out instead of the processing (S101 to S111) of FIG. 9 in the first embodiment described above.

When the sample rack L is placed on the right table 21, the CPU 401 starts the transportation of the sample rack L (S201) and positions the barcode label L3 at the position P1. Then, as shown in FIG. 12A, the CPU 401 reads the rack ID from the barcode label L3 with the barcode reader 54 (S202). The CPU 401 subsequently determines whether the reading of the rack ID by the barcode reader 54 is successful (S203). The process proceeds to S204 if the reading of the rack ID is successful (S203: YES), and the process proceeds to S209 if the reading of the rack ID is failure (S203: NO).

In S204, the CPU 401 determines whether the registered information corresponding to the read rack ID is registered in a registered information table shown in FIG. 14A. The registered information table is stored in the hard disk 404, and includes an item indicating a predetermined range (e.g., three leading digits) of the rack ID, and an item indicating a type of sample rack L. Only the special rack is registered in the registered information table of the present embodiment. In other words, only a predetermined range of the rack ID included in the barcode label L3 attached to the special rack is registered in the item indicating the predetermined range of the rack ID, and only "special rack" is registered in the item indicating the type of sample rack L.

If the predetermined range of the rack ID read in S202 is registered in the registered information table (S204: YES), the CPU 401 determines that the sample rack L is the special rack (S205). The CPU 401 then performs detection by the sensors s2, s3 with respect to the holding positions n2 to n10 (S206). If the predetermined range of the rack ID read in S202 is not registered in the registered information table (S204: NO), on the other hand, the CPU 401 determines that the sample rack L is the normal rack (S207). The CPU 401 then performs detection by the sensors s2, s3 with respect to the holding positions n1 to n10 (S208). In S206, S208, the reading of the sample ID by the barcode reader 54 is also appropriately carried out.

If the reading of the rack ID fails (S203: NO), the type of sample rack L is distinguished (S209 to S216), similar to S102 to S109 of the first embodiment described above, using the sensors s3, s2 in place of the sensors s1, s2 of the first embodiment described above. If the detection result of the sensor s3 is "sample container present" (S210: YES), the reading of the sample ID by the barcode reader 54 is carried out with respect to the holding position n1. The CPU 401 then performs detection by the sensors s2, s3 with respect to the holding positions n2 to n10 (S217). In S217 as well, the reading of the sample ID by the barcode reader 54 is also appropriately carried out.

The CPU 401 then determines the necessity of sample processing with respect to the holding positions n1 to n10, similar to the first embodiment, based on the detection results of the sensors s2, s3 in S206, S208, S209, S217 (S218). The process then proceeds to S112 of FIG. 10, similar to the embodiment described above.

According to the present embodiment, if the reading of the rack ID by the barcode reader 54 is successful (S203: YES), the type of sample rack L is determined based on the read rack ID (S204). Since the type of sample container held in the sample rack L can be distinguished, the stirring operation and the aspirating operation on the sample container can be appropriately carried out according to the distinguished type of sample container. Furthermore, if the reading of the rack ID by the barcode reader 54 is failure (S203: NO), the type of sample rack L is determined based on the presence/absence of the rack distinction member J, and hence the type of sample container held in the sample rack L can be distinguished, similar to the embodiment described above. The stirring operation and the aspirating operation with respect to the sample container thus can be appropriately carried out according to the distinguished type of sample container.

The first and second embodiments of the present invention have been described above, but the present invention is not limited thereto.

For example, only the predetermined range of the rack ID is registered in the registered information table of the second embodiment, but instead, the entire range of the rack ID may be registered. In this case, whether or not the entire range of the rack ID read by the barcode reader 54 is registered in the registered information table is determined in S204.

In the second embodiment described above, the sample rack L is determined as normal rack (S207) if the predetermined range of the read rack ID is not registered in the registered information table (S204: NO). However, this is not the sole case, and if the predetermined range of the read rack ID is not registered in the registered information table (S204: NO), as shown in FIG. 14B, the process proceeds to S209 and the type of sample rack L is distinguished based on the presence/absence of the rack distinction member J.

According to a variant shown in FIG. 14B, the type of sample rack L is distinguished based on the presence/absence of the rack distinction member J even if the predetermined range of the rack ID of the sample rack L is not registered in the registered information table shown in FIG. 14A although the sample rack L is the special rack. Thus, the aspirating operation with respect to the sample container T1 is not carried out by mistake with respect to the sample container T2 held in the special rack, which failed to be registered by accident, whereby the bottom surface T21a of the sample container T2 and the piercer 34a are avoided from being damaged.

Figure 15A:
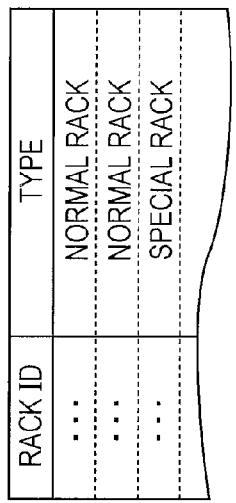
FIGS. 15A through 15C are conceptual diagrams showing a configuration of a registered information table according to the variant, and a flowchart showing processing by the information processing unit according to the variant.

Only the rack ID of the special rack is registered in the registered information table of the second embodiment described above, but this is not the sole case, and the rack ID of the normal rack may also be registered, as shown in FIG. 15A.

Figure 15C:
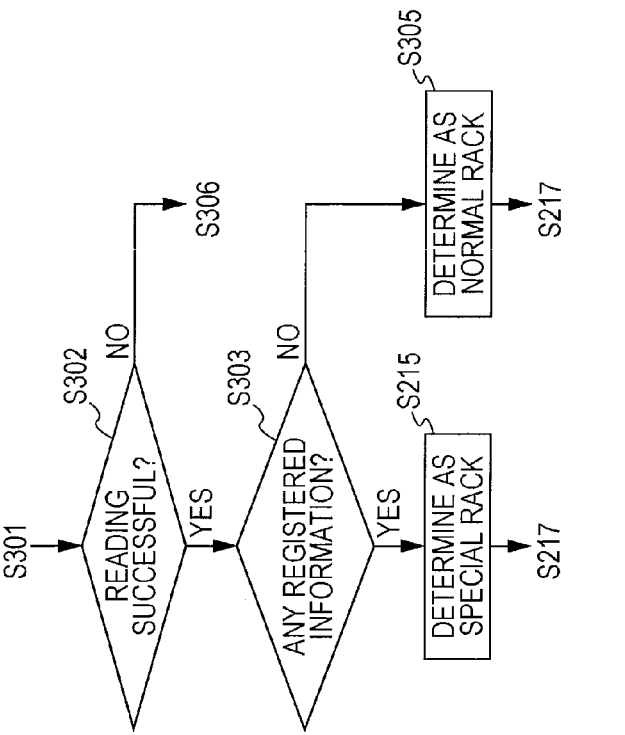
Figure 15B:
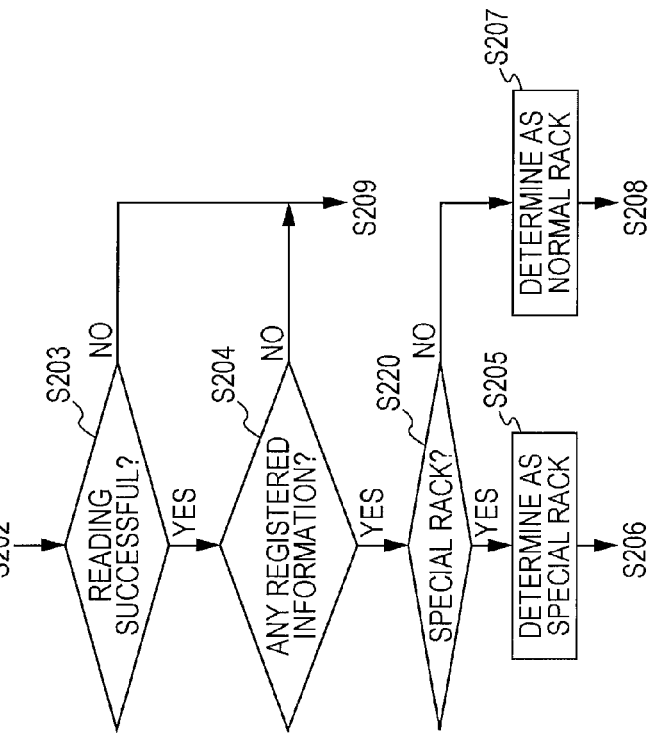

FIG. 15B is a view showing a flowchart for this case. FIG. 15B is a view showing a part of the flowchart shown in FIG. 13, where S220 is added to the post-stage of S204 of FIG. 13 in FIG. 15B.

If the predetermined range of the read rack ID is registered in the registered information table (S204: YES), the CPU 401 references the registered information table and acquires the type of sample rack L. The CPU 401 determines that the sample rack L is the special rack (S205) if the acquired type of sample rack L is the special rack (S220: YES), and determines that the sample rack L is the normal rack (S207) if the acquired type of sample rack L is the normal rack (S220: NO). If the predetermined range of the read rack ID is not registered in the registered information table (S204: NO), on the other hand, the process proceeds to S209, and the type of sample rack L is distinguished based on the presence/absence of the rack distinction member J.

According to the variant shown in FIGS. 15A and 15B, the type of sample container held in the sample rack L can be distinguished based on the presence/absence of the rack distinction member J even if the rack ID read by the barcode reader 54 is not registered in the registered information table, and hence the stirring operation and the aspirating operation with respect to the sample container can be appropriately carried out.

In the second embodiment described above, the type of sample rack L is distinguished based on the rack ID as a normal operation, and the type of sample rack L is distinguished based on the presence/absence of the rack distinction member J only if the reading of the rack ID fails. However, this is not the sole case, and the type of sample rack L may be distinguished based on the presence/absence of the rack distinction member J as the normal operation, and the type of sample rack L may be distinguished based on the rack ID only if detected that the rack distinction member J is not held.

FIG. 16 is a view showing a flowchart for this case. In FIG. 16, S209 to S218 are moved to the post-stage of S201, and the process proceeds to S301 to S306 when determined as the normal rack (S212, S213, S216) in the flowchart shown in FIG. 13. The registered information table in this case has the rack ID of the normal rack registered, as shown in FIG. 15A.

When the process proceeds to S301, the CPU 401 positions the barcode label L3 at the position P1, and reads the rack ID with the barcode reader 54 (S301). If the reading of the rack ID is successful (S302: YES), the CPU 401 references the registered information table and acquires the type of rack corresponding to the read rack ID. If the acquired type of sample rack L is the normal rack (S304: YES), that is, if the result is the same as the determination (S212, S213, S216) based on the presence/absence of the rack distinction member J, the CPU 401 determines that the sample rack L is the normal rack L (S305), and proceeds the process to S217.

If the reading is failure (S302: NO), a warning is displayed on the display unit 41 (S306), the sample rack L is transported to the left table 22, and the process is terminated. The process also proceeds to S306 if a predetermined range of the read rack ID is not registered in the registered information table (S303: NO). The process also proceeds to S306 if the type of rack corresponding to the read rack ID is acquired but the type of racks is the special rack (S304: NO), that is, if the result is different from the determination based on the presence/absence of the rack distinction member J.

According to the variant shown in FIG. 16, if the rack ID of the sample rack L not holding the rack distinction member J is registered as the special rack in the registered information table, the sample container T2 being held in the relevant sample rack L can be prevented from being mistakenly processed as the sample container T1.

For example, consider a case where the user takes out the sample rack L not holding the rack distinction member J, registers the rack ID of the relevant sample rack L as the special rack in the registered information table, and forgets to install the rack distinction member J. In this case, when the distinction of the type of sample rack L is carried out according to the first embodiment, the sample rack L is distinguished as the normal rack since the rack distinction member J is not held. If the user sets the sample container T2 in the relevant sample rack L, the sample container T2 is subjected to the aspirating operation similar to the sample container T1, and thus the bottom surface T21a of the sample container T2 and the piercer 34a may be damaged. However, according to the variant shown in FIG. 16, the determination based on the rack ID is further carried out after the determination by the rack distinction member J, and thus the bottom surface T21a and the piercer 34a are avoided from being damaged.

In FIG. 16, the registered information table registers the rack ID of the normal rack, as shown in FIG. 15A, but may register only the rack ID of the special rack, as shown in FIG. 14A. In this case, as shown in FIG. 15C, the sample rack L is determined as the special rack (S215) if the predetermined range of the read rack ID is registered in the registered information table (S303: YES), and the sample rack L is determined as the normal rack (S305) if the predetermined range of the read rack ID is not registered in the registered information table (S303: NO).

According to the embodiment described above, the rack distinction member J is configured so as not to transmit light, but may be configured such that the transmissivity is a predetermined value. For example, a rack distinction member J10, in which the transmissivity is set such that some light emitted from the sensor s2 transmits therethrough, may be installed in the sample rack L, as shown in FIG. 17A. For example, if the transmissivity becomes larger in the order of the sample container T1 containing sample, the rack distinction member J10, and the sample container T1 not containing sample, the determination on the presence/absence of the rack distinction member J10 may be carried out by using only the sensor s2 without using the sensor s1 in the first embodiment described above.

FIG. 17B is a flowchart showing the process for this case. FIG. 17B is a view showing a part of the flowchart shown in FIG. 9, where S401 to S407 are added in place of S102 to S110 of FIG. 9 in FIG. 17B. If the light emitted from the light emitting portion of the sensor s2 transmits through the sample container T1 containing sample, the rack distinction member J10, and the sample container T1 not containing sample, the light receiving amount of the sensor s2 becomes smaller than r1, greater than or equal to r1 and smaller than r2, and greater than or equal to r2, respectively.

First, the detection by the sensor s2 is carried out with respect to the holding position n1 (S401). If the light receiving amount of the light receiving portion of the sensor s2 is smaller than r1 (S402: YES), the sample rack L is determined as the normal rack (S403) since the sample container T1 containing sample is held at the holding position n1. If the light receiving amount of the light receiving portion of the sensor s2 is greater than or equal to r1 and smaller than r2 (S404: YES), the sample rack L is determined as the special rack (S405) since the rack distinction member J10 is held at the holding position n1. If the light receiving amount of the light receiving portion of the sensor s2 is greater than or equal to r2 (S404: NO), the sample rack L is determined as the normal rack L (S406) since the sample container T1 not containing sample is held or nothing is held at the holding position n1. The detection by the sensors s1, s2 is then carried out with respect to the holding positions n1 to n10 (S407).

Assuming the sample racks L in which the rack distinction members J11, J12 are installed at the holding position n1 shown in FIGS. 18A, 18B are special racks v1, v2, and the transmissivity becomes greater in the order of the sample container T1 containing sample, the rack distinction member J11, the rack distinction member J12, and the sample container T1 not containing sample, the presence/absence of the rack distinction members J11, J12 can be determined and whether the sample rack L is the special rack v1 or v2 can be determined by using only the sensor s2 without using the sensor s1.

FIG. 18C is a flowchart showing the process for this case. In FIG. 18C, S411 to S413 are added in place of S405 of FIG. 17B. If the light emitted from the light emitting portion of the sensor s2 transmits through the sample container T1 containing sample, the rack distinction member J11, the rack distinction member J12, and the sample container T1 not containing sample, the light receiving amount of the sensor s2 becomes smaller than r1, greater than or equal to r1 and smaller than r2, greater than or equal to r2 and smaller than r3, and greater than or equal to r3, respectively.

In this case, if the light receiving amount of the light receiving portion of the sensor s2 is greater than or equal to r1 and smaller than r2 (S404: YES), the sample rack L is determined as the special rack v1 (S411) since the rack distinction member J11 is held at the holding position n1. If the light receiving amount of the light receiving portion of the sensor s2 is greater than or equal to r2 and smaller than r3 (S412: YES), the sample rack L is determined as the special rack v2 (S413) since the rack distinction member J12 is held at the holding position n1.

According to the variant shown in FIGS. 18A to 18C, whether the rack distinction member installed at the holding position n1 is the rack distinction member J11 or the rack distinction member J12 can be distinguished along with the presence/absence of the rack distinction member at the holding position n1 of the sample rack L. Thus, if the sample container corresponding to the special rack v1, v2 is held, the type of sample container can be distinguished according to the type of distinguished sample rack L.

If the rack distinction member J is configured to include a plurality of regions with different transmissivity, a plurality of special racks can be further distinguished.

Figure 19A:
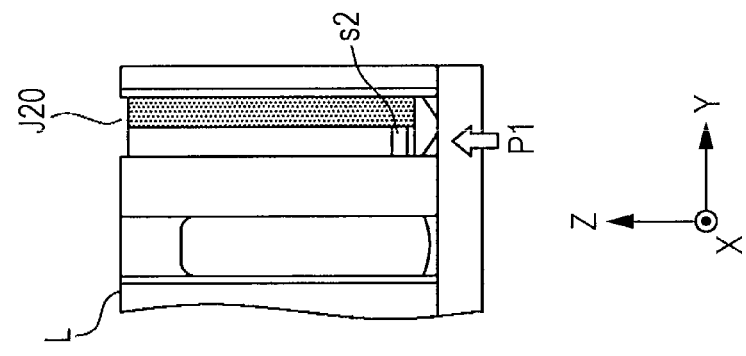
FIGS. 19A through 19C are views describing a configuration of the rack distinction member and detection by a sensor according to the variant.

FIG. 19A is a view showing a configuration of a rack distinction member J20, in which the transmissivity of the region on the right side when facing front is set to t1, in the rack distinction member J of the embodiment described above. The sample rack L in which the rack distinction member J20 is installed such that the region having the transmissivity t1 is positioned on the positive direction side of the Y axis of the holding position n1 is assumed as a special rack v3, and the sample rack L in which the rack distinction member J20 is installed such that the region having the transmissivity t1 is positioned on the negative direction side of the Y axis of the holding position n1 is assumed as a special rack v4.

Figure 19B:
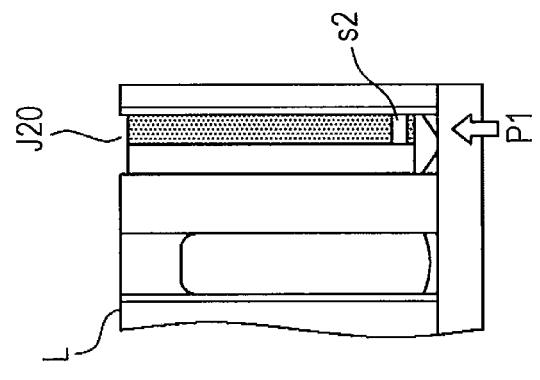
Figure 19C:
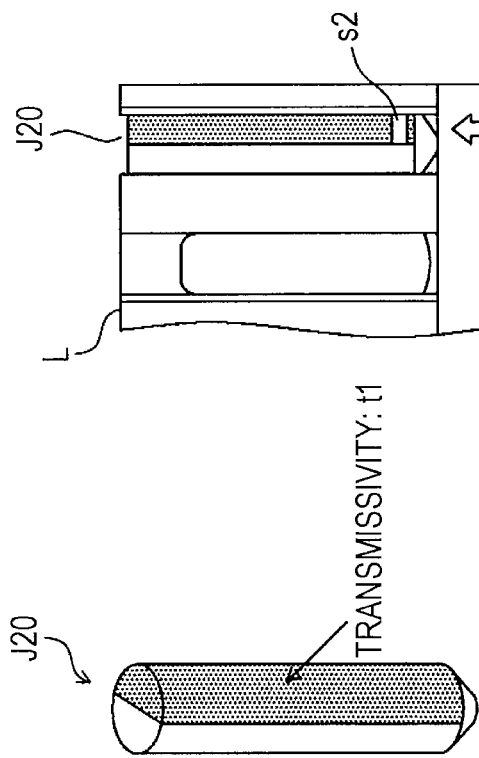

The detection of the sensor s2 with respect to the holding position n1 of such special racks v3, v4 is carried out with respect to the right half and the left half of the holding position n1. In other words, the detection of the sensor s2 is performed such that the sample rack L is finely moved to the left and right (Y axis direction), where the detection is first carried out on the right half of the holding position n1 (positive direction side in the Y axis), as shown in FIG. 19B, and then carried out on the left half of the holding position n1 (negative direction side in the Y axis), as shown in FIG. 19C. Since the detection of the sensor s2 is carried out on the right half and the left half of the holding position n1, whether the sample rack L is the special rack v3 or v4 can be distinguished.

In the embodiment described above, the rack distinction member J is installed only at the holding position n1 of the sample rack L, but this is not the sole case, and a plurality of special racks may be distinguished by installing the rack distinction member J in at least one of the two or more holding positions.

FIGS. 20A to 20D are views showing the special racks v5 to v7 and the normal rack. In the special racks v5 to v7, the rack distinction member J is installed in at least one of the two holding positions. FIG. 20E is view showing a flowchart for this case. In FIG. 20E, S501 to S509 are added in place of S102 to S110 in the flowchart shown in FIG. 9.

The CPU 401 performs detection by the sensors s1, s2 on the holding positions n1, n2 (S501). If the rack distinction member J is at the holding position n1, n2 (S502: YES, S503: YES), the CPU 401 determines that the sample rack L is a special rack v5 (S504). If the rack distinction member J is installed at the holding position n1 (S502: YES) but the rack distinction member J is not installed at the holding position n2 (S503: NO), the CPU 401 determines that the sample rack L is a special rack v6 (S505). If the rack distinction member J is not installed at the holding position n1 (S502: NO) but the rack distinction member J is installed at the holding position n2 (S506: YES), the CPU 401 determines that the sample rack L is a special rack v7 (S507). If the rack distinction member J is not installed at either holding position n1, n2 (S502: NO, S506: NO), the CPU 401 determines that the sample rack L is the normal rack (S508). The CPU 401 then performs detection by the sensors s1, s2 on the holding positions n3 to n10 (S509).

According to the variant shown in FIGS. 20A to 20E, which one of the special racks v5 to v7 and the normal rack is the sample rack L can be determined. Thus, if the sample container corresponding to the special racks v5 to v7 is held, the type of sample container can be distinguished according to the type of distinguished sample rack L.

In the embodiment described above, the rack distinction member J may be configured to have a metal portion. In this case, for example, the presence or absence of the rack distinction member J at the holding position n1 can be detected based on the detection signal of the metal sensor if the metal sensor is installed in the vicinity of the position P1.

FIG. 21A is a flowchart showing the process for this case. In FIG. 21A, S601 to S606 are added in place of S102 to S110 in the flowchart shown in FIG. 9. When the detection by the metal sensor is carried out on the holding position n1 by the CPU 401 (S601), the presence/absence of the rack distinction member J at the holding position n1 is detected. If the rack distinction member J1 is at the holding position n1 (S602: YES), the sample rack L is determined as the special rack (S603), and the detection by the sensors s1, s2 is carried out on the holding positions n2 to n10 (S604). If the rack distinction member J1 is not at the holding position n1 (S602: NO), the sample rack L is determined as the normal rack (S605), and the detection by the sensors s1, s2 is carried out on the holding positions n1 to n10 (S606).

In the embodiment described above, the rack distinction member J may be configured to have a magnetic portion. In this case, for example, the presence or absence of the rack distinction member J at the holding position n1 can be detected based on the detection signal of the hall element if the hall element is installed in the vicinity of the position P1.

FIG. 21B is a flowchart showing the process for this case. In FIG. 21B, S611 is added in place of S601 in the flowchart shown in FIG. 21(a). When the detection by the hall element is carried out on the holding position n1 by the CPU 401 (S611), the presence/absence of the rack distinction member J at the holding position n1 is detected. The type of sample rack L is thereby distinguished, similar to FIG. 21A.

In the embodiment described above, the rack distinction member J may be configured such that the outer appearance has a predetermined color. In this case, for example, the presence or absence of the rack distinction member J at the holding position n1 can be detected based on the detection signal of the color sensor and the imaging mechanism if the color sensor and the imaging mechanism are installed in the vicinity of the position P1.

FIG. 21C is a flowchart showing the process for a case in which the color sensor is used. In FIG. 21C, S612 is added in place of S601 in the flowchart shown in FIG. 21A. When the detection by the color sensor is carried out on the holding position n1 by the CPU 401 (S612), the presence/absence of the rack distinction member J at the holding position n1 is detected. The type of sample rack L is thereby distinguished, similar to FIG. 21A.

In the embodiment described above, the numbers of turnovers of the sample containers T1, T2 are fn1, fn2, respectively, in the stirring operation with respect to the sample container, but the strength of turnover (e.g., angular speed of the shaft 31b of the gripping section 31, etc.) may be appropriately set in addition to the number of turnovers.

In the embodiment described above, the necessity of sample processing with respect to each holding position is determined based on the detection results of the sensors s1, s2, but this is not the sole case, and the necessity of sample processing may be determined based on the detection result of only the sensor s1. For example, determination may be made that the sample processing is necessary with respect to the holding position where the detection result of the sensor s1 is "sample container present".

In the embodiment described above, the special rack is configured by having the rack distinction member J installed at the holding position n1 of the sample rack L, but this is not the sole case, and may be configured by installing the rack distinction member J at the holding position different from the holding position n1 of the sample rack L. In this case, the sample container from the head of the transporting direction of the sample rack L up to the holding position where the rack distinction member J is installed may be recognized as the sample container T1, and the sample container after the holding position where the rack distinction member J is installed may be recognized as the sample container T2.

Furthermore, in the embodiment described above, the sensors s1 to s3 are transmissive sensors including the light emitting portion and the light receiving portion, but are not limited thereto, and may be reflective sensors. The sensors s1 to s3 may be sensors based on other principles such as magnetic type, contact type, and the like.

In the embodiment described above, the presence/absence of the rack distinction member J is detected using a plurality of sensors, but a dedicated sensor for detecting the rack distinction member J may be arranged.

In the embodiment described, the presence/absence of the rack distinction member J is detected with a sensor, and the like, but a dedicated barcode may be applied to the surface of the rack distinction member J, and the installation of the rack distinction member J at the holding position of the sample rack L may be detected by reading the barcode with the barcode reader 54 to determine the presence/absence of the rack distinction member J.

In the second embodiment described above, the barcode label L3 is attached as a medium storing the rack ID of the sample rack L, but this is not the sole case, and an RFID tag may be attached. In this case, an antenna that reads information from the RFID tag is installed in place of the barcode reader 54.

In the embodiment described above, the device to apply the present invention is the blood cell analyzer 1, but this is not the sole case. The present invention may be applied to sample processing apparatuses that process samples such as immune analyzer, gene amplification measurement device, biochemical analyzer, urine qualitative analyzer, urine sediment analyzer, blood smear creating apparatus, and the like.

What is claimed is:

1. A sample processing apparatus comprising:
a transporting section configured to transport a first sample rack that holds first sample containers at a plurality of holding positions and a second sample rack that holds second sample containers at a plurality of holding positions and a rack distinction member at a designated holding position of the second sample rack,
the second sample rack being different from the first sample rack without holding the rack distinction member,
each of the second sample containers being different from each of the first sample containers,
each of the first and second sample containers being a tubular container made of glass or synthetic resin having translucency, and
the rack distinction member having lower translucency than that of each of the first and second sample containers and having shorter length than that of each of the first and second sample containers;
a detecting section configured to detect a presence or an absence of the rack distinction member at the designated holding position of the transported first or second sample rack;
an aspirating section configured to aspirate a sample in each of the first and second sample containers and including a piercer for aspirating the sample and a driver for driving the piercer in the up and down direction; and
a control section configured to control an aspirating operation of the aspirating section based on the presence or the absence of the rack distinction member at the designated holding position,
wherein the piercer is driven in the downward direction for the aspirating operation of the aspirating section so that the tip of the piercer is positioned at a first position when the detecting section detects the absence of the rack distinction member at the designated holding position, and
the piercer is driven in the downward direction for the aspirating operation so that the tip of the piercer is positioned at a second position different from the first position when the detecting section detects the presence of the rack distinction member at the designated holding position.

2. The sample processing apparatus according to claim 1, further comprising a stirring section that grips and stirs the first or second sample container, wherein the control section controls the stirring section so as to execute a first stirring operation based on the absence of the rack distinction member, and controls the stirring section so as to execute a second stirring operation different from the first stirring operation based on the presence of the rack distinction member.

3. The sample processing apparatus according to claim 1, wherein the control section controls the aspirating section to perform the same aspirating operation on all of the first sample containers held in the first sample rack based on the absence of the rack distinction member and perform the same aspirating operation on all of the second sample containers held in the second sample rack based on the presence of the rack distinction member.

4. The sample processing apparatus according to claim 1, wherein the detecting section includes a first detecting section configured to detect a presence or absence of each of the first and second sample containers at the designated holding position held in each of the first and second sample racks, and a second detecting section configured to detect whether or not a sample is contained in each of the first and second sample containers at the designated holding position held in each of the first and second sample racks; and the control section distinguishes the presence or absence of the rack distinction member based on the detection results of the first detecting section and the second detecting section.

5. The sample processing apparatus according to claim 4, wherein when the detection result of the first detecting section detects is absent and the detection result of the second detecting section detects is present, the control section distinguishes that the rack distinction member is present.

6. The sample processing apparatus according to claim 4, wherein the first detecting section and the second detecting section detect the presence or absence of a detection target at different heights.

7. The sample processing apparatus according to claim 6, wherein the first detecting section distinguishes the presence or absence of the rack distinction member based on a difference of the height of the rack distinction member and a height of the first and second sample containers.

8. The sample processing apparatus according to claim 4, wherein the first detecting section detects the presence or absence of the second sample containers at each holding position of the second sample rack; and
the control section determines a necessity of sample processing with respect to the holding position based on the presence or absence of the second sample container at each holding position.

9. The sample processing apparatus according to claim 4, wherein the second detecting section detects whether or not a sample is contained in the sample container at each holding position of the sample rack; and
the control section determines a necessity of sample processing with respect to the holding position based on the presence or absence of the predetermined amount of sample in the sample containers at each holding position.

10. The sample processing apparatus according to claim 1, further comprising an acquiring unit configured to acquire container information from a recording unit, which is arranged in each of the first and second sample racks and which is recorded with the container information that specifies of the first or second sample container held,
wherein the control section controls the aspirating operation based on the container information acquired by the acquiring unit; and
where the container information is not acquired by the acquiring unit, the control section controls the aspirating operation based on the presence or absence of the rack distinction member.

11. The sample processing apparatus according to claim 10, where the container information acquired by the acquiring unit is not registered in a storage unit, the control section controls the aspirating operation based on the presence of the rack distinction member.

12. The sample processing apparatus according to claim 1, further comprising an acquiring unit configured to acquire container information from a recording unit in the first or second sample rack and that is recorded with the container information that specifies the first or second sample container held by the first or second sample rack,
where the rack distinction member is absent, the control section controls the aspirating operation based on the container information acquired by the acquiring unit.

13. The sample processing apparatus according to claim 1, wherein the designated holding position of the rack distinction member in the second sample rack is a leading holding position in a transporting direction from a sample rack inserting section to the aspirating section.

14. The sample processing apparatus according to claim 1, wherein a height of the rack distinction member is less than a height of each of the first and second sample containers, and the second sample container has a smaller capacity than that of the first sample container.

15. The sample processing apparatus according to claim 1, wherein the first position is a position where the tip of the piercer is close to the inner bottom of the first sample container, and the second position is a position where the tip of the piercer is close to the inner bottom of the second sample container.

16. The sample processing apparatus according to claim 1, wherein the first position is a position where the tip of the piercer is in contact with the inner bottom of the first sample container, and the second position is a position where the tip of the piercer is in contact with the inner bottom of the second sample container.

17. A sample processing method comprising:
providing a first sample rack that holds first sample containers in a plurality of holding positions and a second sample rack that holds second sample containers at a plurality of holding positions and a rack distinction member in a designated holding position of the second sample rack, the second sample rack being different from the first sample rack without holding the rack distinction member, each of the second sample containers different from each of the first sample containers, each of the first and second sample containers being a tubular container made of glass or synthetic resin having translucency, and the rack distinction member having lower translucency than that of each of the first and second sample containers and having shorter length than that of each of the first and second sample containers;
transporting the first or second sample rack to a predetermined position;
distinguishing a presence or absence of the rack distinction member at the designated holding position of the first or second sample rack transported to the predetermined position; and
aspirating a sample in the first or second sample container using an aspirator having a piercer for aspirating the sample,
wherein the piercer is driven in the downward direction for an aspirating operation so that the tip of the piercer is positioned at a first position when the rack distinction member is absent in the designated holding position, and
the piercer is driven in the downward direction for the aspirating operation so that the tip of the piercer is positioned at a second position different from the first position when the rack distinction member is present in the designated holding position.

18. The sample processing method according to claim 17, further comprising stirring the first or second sample container, wherein a first stirring operation with respect to the first sample container held in the first sample rack is executed based on the absence of the rack distinction member, and a second stirring operation different from the first stirring operation with respect to the second sample container held in the second sample rack is executed based on the presence of the rack distinction member.

19. The sample processing method according to claim 17, wherein the aspirator performs the same aspirating operation on all of the first sample containers held in the first sample rack based on the absence of the rack distinction member and perform the same aspirating operation on all of the second sample containers held in the second sample rack based on the presence of the rack distinction member.

20. The sample processing method according to claim 17, and the second sample container has a smaller capacity than that of the first sample container.

21. The sample processing method according to claim 17, wherein the first position is a position where the tip of the piercer is close to the inner bottom of the first sample container, and the second position is a position where the tip of the piercer is close to the inner bottom of the second sample container.

22. The sample processing method according to claim 17, wherein the first position is a position where the tip of the piercer is in contact with the inner bottom of the first sample container, and the second position is a position where the tip of the piercer is in contact with the inner bottom of the second sample container.

* * * * *